United States Patent
Hakimi et al.

(10) Patent No.: US 7,122,719 B2
(45) Date of Patent: Oct. 17, 2006

(54) METHOD OF IMPARTING DISEASE RESISTANCE TO PLANTS BY REDUCING POLYPHENOL OXIDASE ACTIVITIES

(75) Inventors: Salim M. Hakimi, West Des Moines, IA (US); Bradley M. Krohn, Ballwin, MO (US); David M. Stark, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 93 days.

(21) Appl. No.: 10/415,759

(22) PCT Filed: Nov. 2, 2001

(86) PCT No.: PCT/US01/50427

§ 371 (c)(1),
(2), (4) Date: Aug. 18, 2003

(87) PCT Pub. No.: WO02/061101

PCT Pub. Date: Aug. 8, 2002

(65) Prior Publication Data

US 2005/0101484 A1    May 12, 2005

Related U.S. Application Data

(60) Provisional application No. 60/245,876, filed on Nov. 3, 2000.

(51) Int. Cl.
  *C12N 15/09* (2006.01)
  *C12N 15/29* (2006.01)
  *C12N 15/82* (2006.01)
  *A01H 5/00* (2006.01)
  *A01H 5/10* (2006.01)

(52) U.S. Cl. ................. 800/279; 800/278; 800/317.2; 800/298; 800/295; 435/468; 435/419

(58) Field of Classification Search ............... 800/278, 800/279, 298, 295, 317, 317.2; 435/468, 435/69.1, 419
See application file for complete search history.

(56) References Cited

U.S. PATENT DOCUMENTS 6,160,204 A * 12/2000 Steffens ..................... 800/284
6,936,748 B1   8/2005 Robinson et al.

FOREIGN PATENT DOCUMENTS

| WO | WO 93 15599 A | 8/1993 |
| WO | WO 94 03607 A | 2/1994 |
| WO | WO 99 07865 A | 2/1999 |

OTHER PUBLICATIONS

Smith et al. Nature, vol. 334, pp. 724-726 (1988).*
Carey et al . Journal of Experimental Botany (2001) 52(357) 663-668.*
Napoli et al. The Plant Cell, vol. 2, pp. 279-289, (1990).*

* cited by examiner

*Primary Examiner*—Medina A. Ibrahim
(74) *Attorney, Agent, or Firm*—Timothy K. Ball

(57) ABSTRACT

The present invention relates to a method for enhancing a plant's resistance to diseases and/or bruising by transforming the plant with sense and antisense polyphenol oxidase encoding sequences from potato. The invention also relates to transgenic plants and progeny thereof with reduced polyphenol oxidase activity.

8 Claims, 5 Drawing Sheets

SEQUENCE LISTING

<160> NUMBER OF SEQ ID NOS: 3

<210> SEQ ID NO 1
<211> LENGTH: 1802
<212> TYPE: DNA
<213> ORGANISM: Solanum tuberosum

<400> SEQUENCE: 1

```
ccatggcaag cttgtgcaat agtagtagta catctctcaa aactcctttt acttcttcct      60
ccacttcttt atcttccact cctaagccct ctcaactttt catccatgga aaacgtaacc     120
aaatgttcaa agtttcatgc aaggttacca ataataacgg tgaccaaaac caaaacgttg     180
aaacgaattc tgttgatcga agaaatgttc ttcttggctt aggtggtctt tatggtgttg     240
ctaatgctat accattagct gcatccgctg ctccagctcc acctcctgat ctctcgtctt     300
gtagtatagc caggattaac gaaaatcagg tggtgccgta cagttgttgc gcgcctaagc     360
ctgatgatat ggagaaagtt ccgtattaca agttcccttc tatgaataag ctccgtgttc     420
gtcagcctgc tcatgaagct aatgaggagt atattgccaa gtacaatttg gcggttagca     480
agatgaggga tcttgataag acacaacctt taaaccctat tggttttaag caacaagcta     540
atatacattg tgcttattgt aacggtgctt atagaattgg tggcaaagag ttacaagttc     600
ataattcttg gcttttcttc ccgttccata gatggtactt gtacttctac gagagaatcg     660
```

-continued

```
tgggaaaact cattgatgat gcaactttcg ctttgccata ttggaattgg gaccatccaa      720
agggtatgcg ttttcctgcc atgtatgatc gtgaagggac ttcccttttc gatgtaacac      780
gtgaccaaag tcaccgaaat ggagcagtaa tcgatcttgg ttttatcggc aatgaagtcg      840
aaacaactca actccagttg atgagcaata atttaacact aatgtaccgt caaatggtaa      900
ctaatgctcc atgtcctcgg atgttctttg gcgggcctta tgatctcggg gttaacactg      960
aactcccggg aactatagaa acatccctc acggtcctgt ccacatctgg tctggtacag     1020
tgagaggttc aactttgccc aatggtgcaa tatcaaacgg tgagaatatg ggtcattttt     1080
actcagctgg tttggacccg gttttctttt gccatcacag caatgtggat cggatgtgga     1140
gcgaatggaa agcgacagga gggaaaagaa cggatatcac acataaagat tggttgaact     1200
ccgagttctt tttctatgat gaaaatgaaa acccttaccg tgtgaaagtc agagactgtt     1260
tggacacgaa gaagatggga tacgattaca aaccaattgc cacaccatgg cgtaacttca     1320
agcccttaac aaaggcttca gctggaaaag tgaatacagc ttcacttccg ccagctagca     1380
atgtattccc attggctaaa ctcgacaaag caatttcgtt ttccatcaat aggccgactt     1440
cgtcaaggac tcaacaagag aaaaatgcac aagaggagat gttgacattc agtagcataa     1500
gatatgataa cagagggtac ataaggttcg atgtgttcct gaacgtggac aataatgtga     1560
atgcgaatga gcttgacaag gcggagtttg cggggagtta tacaagtttg ccacatgttc     1620
atagagctgg tgagactaat catatcgcga ctgttgattt ccagctggcg ataacggaac     1680
tgttggagga tattggtttg gaagatgaag atactgttgc ggtgactctg gtgccaaaga     1740
gaggtggtga aggtatctcc attgaaggtg cgacgatcag tcttgcagat tgttaagaat     1800
tc                                                                   1802
```

```
<210> SEQ ID NO 2
<211> LENGTH: 1881
<212> TYPE: DNA
<213> ORGANISM: Solanum tuberosum

<400> SEQUENCE: 2
```

```
agatccgaat tcttaacaat ctgcaagact gatcgtcgca ccttcaatgg agataccttc       60
accacctctc tttggcacca gagtcaccgc aacagtatct tcatcttcca aaccaatatc      120
ctccaacagt tccgttatcg ccagctggaa atcaacagtc gcgatatgat tagtctcacc      180
agctctatga acatgtggca aacttgtata actccccgca aactccgcct tgtcaagctc      240
attcgcattc acattattgt ccacgttcag gaacacatcg aaccttatgt accctctgtt      300
atcatatctt atgctactga atgtcaacat ctcctcttgt gcattttttct cttgttgagt      360
ccttgacgaa gtcggcctat tgatggaaaa cgaaattgct ttgtcgagtt tagccaatgg      420
gaatacattg ctagctggcg gaagtgaagc tgtattcact tttccagctg aagcctttgt      480
taagggcttg aagttacgcc atggtgtggc aattggtttg taatcgtatc ccatcttctt      540
cgtgtccaaa cagtctctga cttcacacg gtaagggttt tcattttcat catagaaaaa      600
gaactcggag ttcaaccaat cttttatgtgt gatatccgtt cttttccctc ctgtcgcttt      660
ccattgctc cacatccgat ccacattgct gtgatggcaa agaaaaccg ggtccaaacc      720
agctgagtaa aaatgaccca tattctcacc gtttgatatt gcaccattgg gcaaagttga      780
acctctcact gtaccagacc agatgtggac aggaccgtga gggatgtttt ctatagttcc      840
cgggagttca gtgttaaccc cgagatcata aggcccgcca agaacatcc gaggacatgg      900
```

-continued

```
agcattagtt accatttgac ggtacattag tgttaaatta ttgctcatca actggagttg    960
agttgtttcg acttcattgc cgataaaacc aagatcgatt actgctccat ttcggtgact   1020
ttggtcacgt gttacatcga aaagggaagt cccttcacga tcatacatgg caggaaaacg   1080
catacccttt ggatggtccc aattccaata tggcaaagcg aaagttgcat catcaatgag   1140
ttttcccacg attctctcgt agaagtacaa gtaccatcta tggaacggga agaaaagcca   1200
agaattatga acttgtaact ctttgccacc aattctataa gcaccgttac aataagcaca   1260
atgtatatta gcttgttgct taaaaccaat agggtttaaa ggttgtgtct tatcaagatc   1320
cctcatcttg ctaaccgcca aattgtactt ggcaatatac tcctcattag cttcatgagc   1380
aggctgacga acacggagct tattcataga agggaacttg taatacggaa ctttctccat   1440
atcatcaggc ttaggcgcgc aacaactgta cggcaccacc tgattttcgt taatcctggc   1500
tatactacaa gacgagagat caggaggtgg agctggagca gcggatgcag ctaatggtat   1560
agcattagca acaccataaa gaccacctaa gccaagaaga acatttcttc gatcaacaga   1620
attcgtttca acgttttggt tttggtcacc gttattattg gtaaccttgc atgaaacttt   1680
gaacatttgg ttacgttttc catggatgaa aagttgagag gcttaggag tggaagataa    1740
agaagtggag gaagaagtaa aaggagtttt gagagatgta ctactactat tgcacaagct   1800
tgccatatgc ccatgagtgg ctgcaggaat tcgatatcaa gcttatcgat accgtcgacc   1860
tcgagggggg gcccggtacc g                                             1881

<210> SEQ ID NO 3
<211> LENGTH: 597
<212> TYPE: PRT
<213> ORGANISM: Solanum tuberosum

<400> SEQUENCE: 3

Met Ala Ser Leu Cys Asn Ser Ser Thr Ser Leu Lys Thr Pro Phe
1               5                   10                  15

Thr Ser Ser Thr Ser Leu Ser Ser Thr Pro Lys Pro Ser Gln Leu
                20                  25                  30

Phe Ile His Gly Lys Arg Asn Gln Met Phe Lys Val Ser Cys Lys Val
                35                  40                  45

Thr Asn Asn Gly Asp Gln Asn Gln Asn Val Glu Thr Asn Ser Val
50                  55                  60

Asp Arg Arg Asn Val Leu Leu Gly Leu Gly Leu Tyr Gly Val Ala
65                  70                  75                  80

Asn Ala Ile Pro Leu Ala Ala Ser Ala Ala Pro Ala Pro Pro Asp
                85                  90                  95

Leu Ser Ser Cys Ser Ile Ala Arg Ile Asn Glu Asn Gln Val Val Pro
                100                 105                 110

Tyr Ser Cys Cys Ala Pro Lys Pro Asp Asp Met Glu Lys Val Pro Tyr
                115                 120                 125

Tyr Lys Phe Pro Ser Met Asn Lys Leu Arg Val Arg Gln Pro Ala His
                130                 135                 140

Glu Ala Asn Glu Glu Tyr Ile Ala Lys Tyr Asn Leu Ala Val Ser Lys
145                 150                 155                 160

Met Arg Asp Leu Asp Lys Thr Gln Pro Leu Asn Pro Ile Gly Phe Lys
                165                 170                 175

Gln Gln Ala Asn Ile His Cys Ala Tyr Cys Asn Gly Ala Tyr Arg Ile
                180                 185                 190

Gly Gly Lys Glu Leu Gln Val His Asn Ser Trp Leu Phe Phe Pro Phe
```

-continued

```
                195                 200                 205
His Arg Trp Tyr Leu Tyr Phe Tyr Glu Arg Ile Val Gly Lys Leu Ile
    210                 215                 220

Asp Asp Ala Thr Phe Ala Leu Pro Tyr Trp Asn Trp Asp His Pro Lys
225                 230                 235                 240

Gly Met Arg Phe Pro Ala Met Tyr Asp Arg Glu Gly Thr Ser Leu Phe
                245                 250                 255

Asp Val Thr Arg Asp Gln Ser His Arg Asn Gly Ala Val Ile Asp Leu
                260                 265                 270

Gly Phe Ile Gly Asn Glu Val Glu Thr Thr Gln Leu Gln Leu Met Ser
            275                 280                 285

Asn Asn Leu Thr Leu Met Tyr Arg Gln Met Val Thr Asn Ala Pro Cys
290                 295                 300

Pro Arg Met Phe Phe Gly Gly Pro Tyr Asp Leu Gly Val Asn Thr Glu
305                 310                 315                 320

Leu Pro Gly Thr Ile Glu Asn Ile Pro His Gly Pro Val His Ile Trp
                325                 330                 335

Ser Gly Thr Val Arg Gly Ser Thr Leu Pro Asn Gly Ala Ile Ser Asn
                340                 345                 350

Gly Glu Asn Met Gly His Phe Tyr Ser Ala Gly Leu Asp Pro Val Phe
            355                 360                 365

Phe Cys His His Ser Asn Val Asp Arg Met Trp Ser Glu Trp Lys Ala
370                 375                 380

Thr Gly Gly Lys Arg Thr Asp Ile Thr His Lys Asp Trp Leu Asn Ser
385                 390                 395                 400

Glu Phe Phe Phe Tyr Asp Glu Asn Glu Asn Pro Tyr Arg Val Lys Val
                405                 410                 415

Arg Asp Cys Leu Asp Thr Lys Lys Met Gly Tyr Asp Tyr Lys Pro Ile
                420                 425                 430

Ala Thr Pro Trp Arg Asn Phe Lys Pro Leu Thr Lys Ala Ser Ala Gly
            435                 440                 445

Lys Val Asn Thr Ala Ser Leu Pro Pro Ala Ser Asn Val Phe Pro Leu
450                 455                 460

Ala Lys Leu Asp Lys Ala Ile Ser Phe Ser Ile Asn Arg Pro Thr Ser
465                 470                 475                 480

Ser Arg Thr Gln Gln Glu Lys Asn Ala Gln Glu Met Leu Thr Phe
                485                 490                 495

Ser Ser Ile Arg Tyr Asp Asn Arg Gly Tyr Ile Arg Phe Asp Val Phe
            500                 505                 510

Leu Asn Val Asp Asn Asn Val Asn Ala Asn Glu Leu Asp Lys Ala Glu
            515                 520                 525

Phe Ala Gly Ser Tyr Thr Ser Leu Pro His Val His Arg Ala Gly Glu
            530                 535                 540

Thr Asn His Ile Ala Thr Val Asp Phe Gln Leu Ala Ile Thr Glu Leu
545                 550                 555                 560

Leu Glu Asp Ile Gly Leu Glu Asp Glu Asp Thr Val Ala Val Thr Leu
                565                 570                 575

Val Pro Lys Arg Gly Gly Glu Gly Ile Ser Ile Glu Gly Ala Thr Ile
                580                 585                 590

Ser Leu Ala Asp Cys
            595
```

METHOD OF IMPARTING DISEASE RESISTANCE TO PLANTS BY REDUCING POLYPHENOL OXIDASE ACTIVITIES

This application claims the benefit of U.S. Provisional Application No. 60/245,876, filed Nov. 3, 2000.

BACKGROUND OF THE INVENTION

This invention is in the field of transformed plants, particularly potatoes, which have been rendered resistant to disease, including the very destructive disease known as late blight, caused by *Phytophthora infestans*.

One of the agronomically most important diseases is caused by the fungal pathogen *P. infestans*. In potato it causes late blight disease. Late blight epidemics have caused a persistent threat to potato growers since the Irish Famine in the early 1800s, and late blight has re-emerged as a devastating disease in the United States with the recent establishment of a new clonal lineage of *P. infestans*, designated A2 isolate US-8. During the mid 1990s, this unusually aggressive lineage replaced an earlier predominant lineage within only two years, and has caused severe epidemics since then, resulting in annual potato losses exceeding 100 million dollars. There are currently no cost-effective means of US-8 control because none of the commercially-available cultivars in the United States contain disease resistance (R-) genes against this pathogen, which is also resistant to the fungicide metalaxyl.

The lack of effective R-genes in cultivated potato is due, in part, to the absence of R-gene breeding programs. Such efforts were discouraged by the fact that eleven R-genes from the resistant wild potato species *Solanum demissum* that had been introgressed into potato in the 1960s resulted in temporary control of late blight only (Landeo et al., In: *Phytophthora infestans*. Ed. Dowley L J et al., Bole Press Ltd. Dublin, Ireland, 268–274, 1995). Apparently, the agricultural use of R-genes for late blight control results in the establishment of races that are not recognized by R-genes, through rapid shifts in population dynamics of *P. infestans*.

An important biotechnology strategy to enhance disease resistance in plants is based on the identification and expression of antifungal proteins (AFP's). Reported AFP classes include defensins and other small cysteine-rich peptides, 2S albumins, chitin-binding proteins, lipid transfer proteins, and hydrogen peroxide-generating enzymes (Garcia-Olmedo et al., *Biopolymers* 47: 479–491, 1998). Unfortunately, the constitutive overexpression of AFP's in transgenic plants has not yet resulted in commercially relevant levels of late blight disease control. Thus, none of the conventional breeding and biotechnology approaches have resulted in the generation of potato cultivars displaying durable late blight resistance.

It is well established that the enzyme polyphenol oxidase (PPO) is the enzyme which catalyzes the conversion of phenolic substrates, predominantly tyrosine, to melanin in many plant species. PPO is the major cause of enzymatic browning in higher plant tissues, including that of potato. Polyphenol oxidases are plastid membrane-associated, copper metalloproteins which catalyze the hydroxylation of monophenols to o-diphenols, and the dehydrogenation of o-diphenols to o-diquinones in the presence of oxygen. The quinone products undergo a series of nonenzymatic secondary autooxidation reactions to produce highly reactive electrophiles which form melanin, as well as covalently crosslink with amine groups of cellular proteins, resulting in brown and black pigment production (Newman, et al., Plant Mol. Biol. 21:1035–1051, 1993; Thygesen, et al., Plant Physiol. 109:525–531, 1995). PPO is also present in non-photosynthetic tissues, and in potato tubers PPO is associated with amyloplasts of tuber cells. In potato tubers, the primary phenolic substrate for PPO is tyrosine, which exists at high levels in the free amino acid pool. PPO utilizes organic acids such as chlorogenic acid and caffeic acid much more rapidly than tyrosine, but these substrates exist in potato tubers at significantly lower levels than tyrosine and are therefore not the primary substrates for PPO in the tuber. PPO catalyzes the slow conversion of tyrosine to dihydroxyphenyl-alanine (DOPA), and rapid conversion of DOPA to DOPA quinone, which autooxidizes to form brown and black melanin pigmentation. Enzymatic browning mediated by PPO occurs when tuber tissue is damaged, usually by physical impact or long-term pressure, and loss of intracellular compartmentalization results, thereby allowing PPO to come into contact with tyrosine. In damaged tissue regions with dark melanin formation, commonly referred to as black spot bruises, the cell walls do not need to be broken, only disruption of intracellular membrane integrity is required (Craft, Am. Pot. J. 43: 112–121, 1966; Stark et al., Am. Pot. J. 62: 657–666, 1985; Corsini et al., Am. Pot. J. 69: 423–434, 1992).

In potato tubers, it is the action of the PPO enzyme which leads to the formation of black spot bruises after physical impact or damage to tuber tissue. It is theorized that the reduced expression of PPO, through transformation with a DNA construct in antisense orientation or through transformation and cosuppression, use of a double-stranded mRNA (dsRNA) construct, the simultaneous expression of both sense and antisense RNA, or other effective means of reduced expression of PPO in potatoes will result in reduced susceptibility of tubers to exhibit black spot bruises (see PCT Patent Applications WO 93/02195, 93/15599, and 94/03607).

It has been previously thought that PPO played a role in the plant's innate resistance to disease and therefore that reduced expression of PPO would render the plant more susceptible to disease (see for example WO 93/15599, page 4). However, it has surprisingly been discovered in the present invention that the opposite result is possible, that is, reduced expression of PPO can render a plant more resistant to disease.

SUMMARY

The present invention provides a method for reducing symptoms of disease in plants, which are exposed to disease-causing organisms, by reducing expression of polyphenol oxidase (PPO) to a level sufficient to result in plants which have reduced levels of damage from said disease. In potatoes it is desirable that the PPO level in tubers be reduced. It is preferred that the level of PPO be reduced at least 50 percent, as compared to the same plant that has not been transformed for reduced expression of polyphenol oxidase. It is more preferred that the level of PPO be reduced at least 65 percent. It is more preferred that the level of PPO be reduced at least 70 percent. It is more preferred that the level of PPO be reduced at least 75 percent. It is more preferred that the level of PPO be reduced at least 80 percent. It is more preferred that the level of PPO be reduced at least 85 percent. It is more preferred that the level of PPO be reduced at least 90 percent. It is more preferred that the level of PPO be reduced at least 95 percent. And more preferably that the level of PPO be reduced at least 99 percent as compared to the same plant that has not been transformed for reduced expression of polyphenol oxidase. The reduction in expression can be effected in a number of ways including (1) antisense transgenic constructs for a native gene or DNA sequence for PPO, (2) cosuppression transgenic constructs for a native gene or DNA sequence for PPO using sense orientation of that gene or sequence of a mutant thereof which produces only a non-catalytic protein, (3) transgenic constructs intended to cause a double-stranded mRNA for a PPO DNA sequence as described below, and (4) the simultaneous expression of both sense and antisense mRNA for a PPO DNA sequence.

One exemplary method used in the present invention was the antisense approach, but the invention is not limited to the antisense method in order to reduce expression of PPO. The tubers of the transgenic potato plant produced following the antisense method display reduced visual symptoms of the fungal disease-causing organism *P. infestans*. These tubers may also display enhanced disease resistance against certain other fungal pathogens that infect potato tubers. Other potato fungal pathogens include, but are not limited to, *Spongospora* (powdery scab), *Rhizoctonia* (black scurf), *Fusarium*(dry rot), *Verticillium* (*Verticillium* wilt), *Alternaria* (early blight), *Polyscytalum* (skin spot), *Sclerotium* (white mold), *Rosellinia* (black rot), *Helicobasidium* (violet root rot), *Macrophomina* (charcoal rot), and *Helminthosporium* (silver scurf), and the like.

The PPO levels may also be reduced in other plant species following the methodologies described in the present invention. Such other plants will then have enhanced resistance to fungal pathogens. These fungal pathogens may include, but are not limited to, *Cercospora* sp. and *Monilinia* sp.

In another embodiment of the present invention transgenic potatoes are produced that display an improved anti-bruising trait by employing specific promoters. PPO is the major cause of enzymatic browning in higher plants including potatoes. The formation of black spot bruises is the action of this enzyme in tubers after they are physically damaged. By using the antisense approach to reduce expression of this enzyme to a very low level, the black spot bruises can be greatly limited. As a result, tubers produced with this invention have an excellent anti-bruising trait over tubers that do not have this trait. The promoters used in the present invention may include a TFM7 promoter from tomato fruits, a Sporamin A (SpoA) promoter from sweet potatoes and an ADP-glucose pyrophosphorylase small subunit (smADPGPP) promoter from potatoes.

These and other features, aspects, and advantages of the present invention will become better understood with regard to the following description, appended claims and accompanying figures where:

DESCRIPTION OF SEQUENCES

Figure 1:
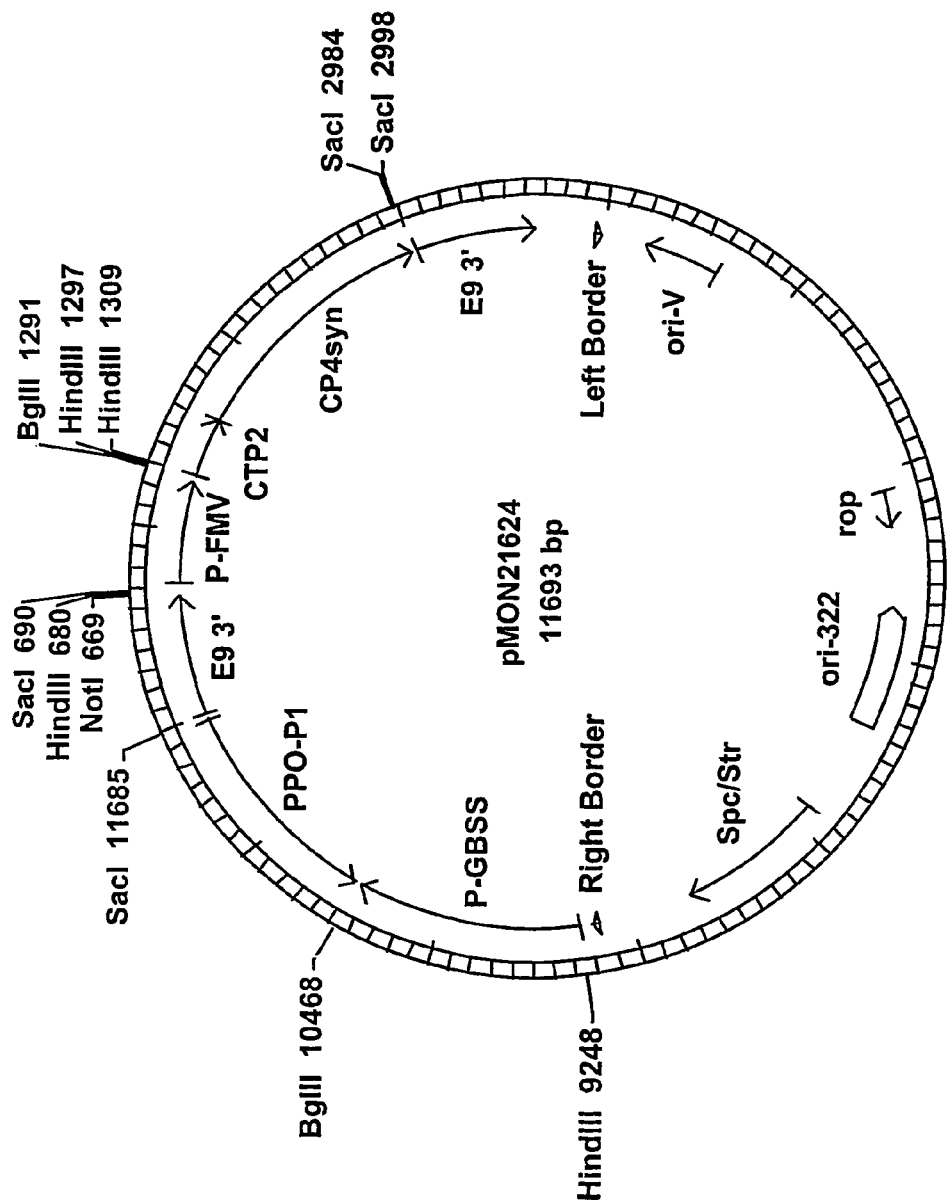
FIG. 1 shows a plasmid map for representation of pMON 21624.
Figure 2:
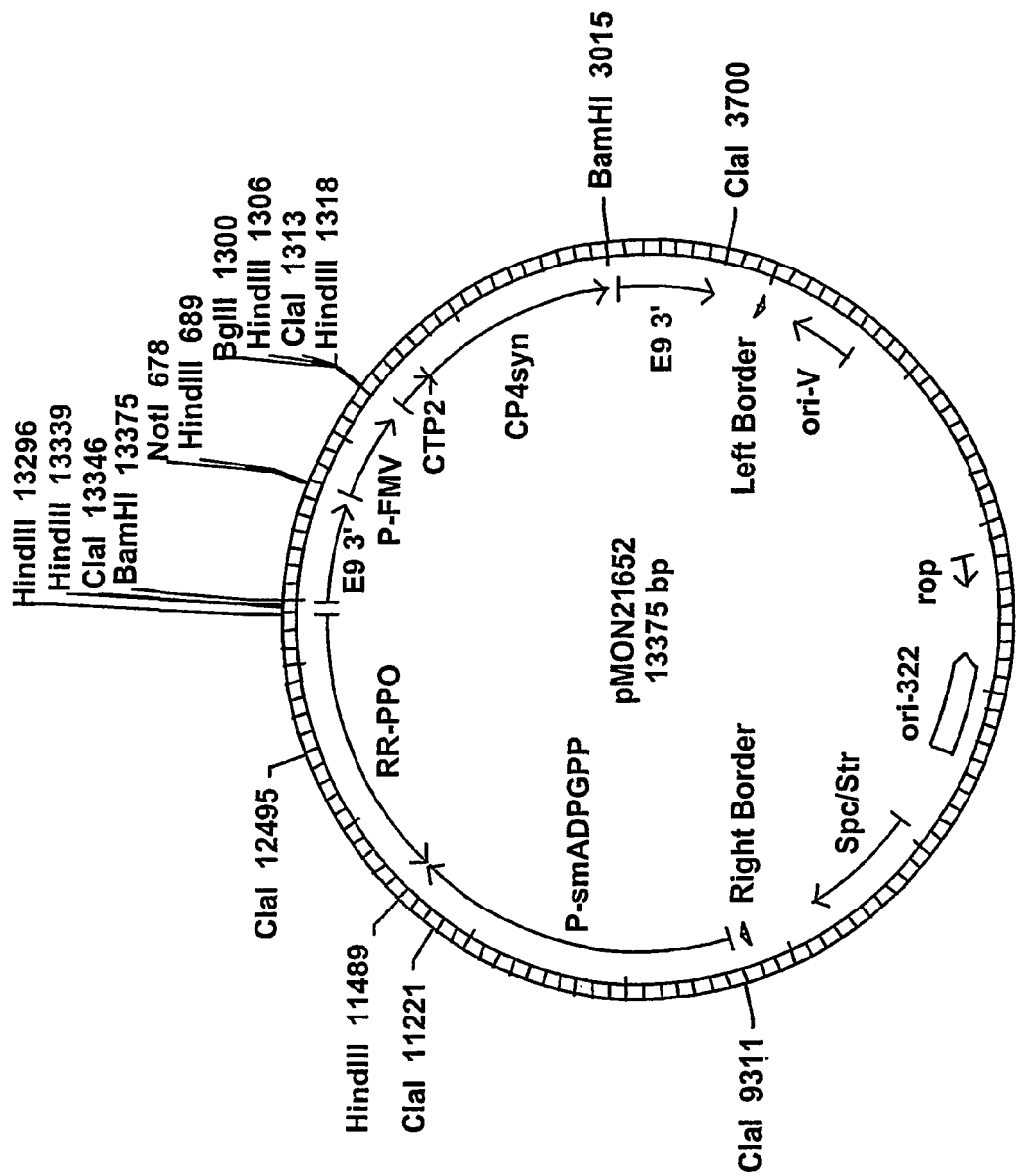
FIG. 2 shows a plasmid map for representation of pMON 21652.
Figure 3:
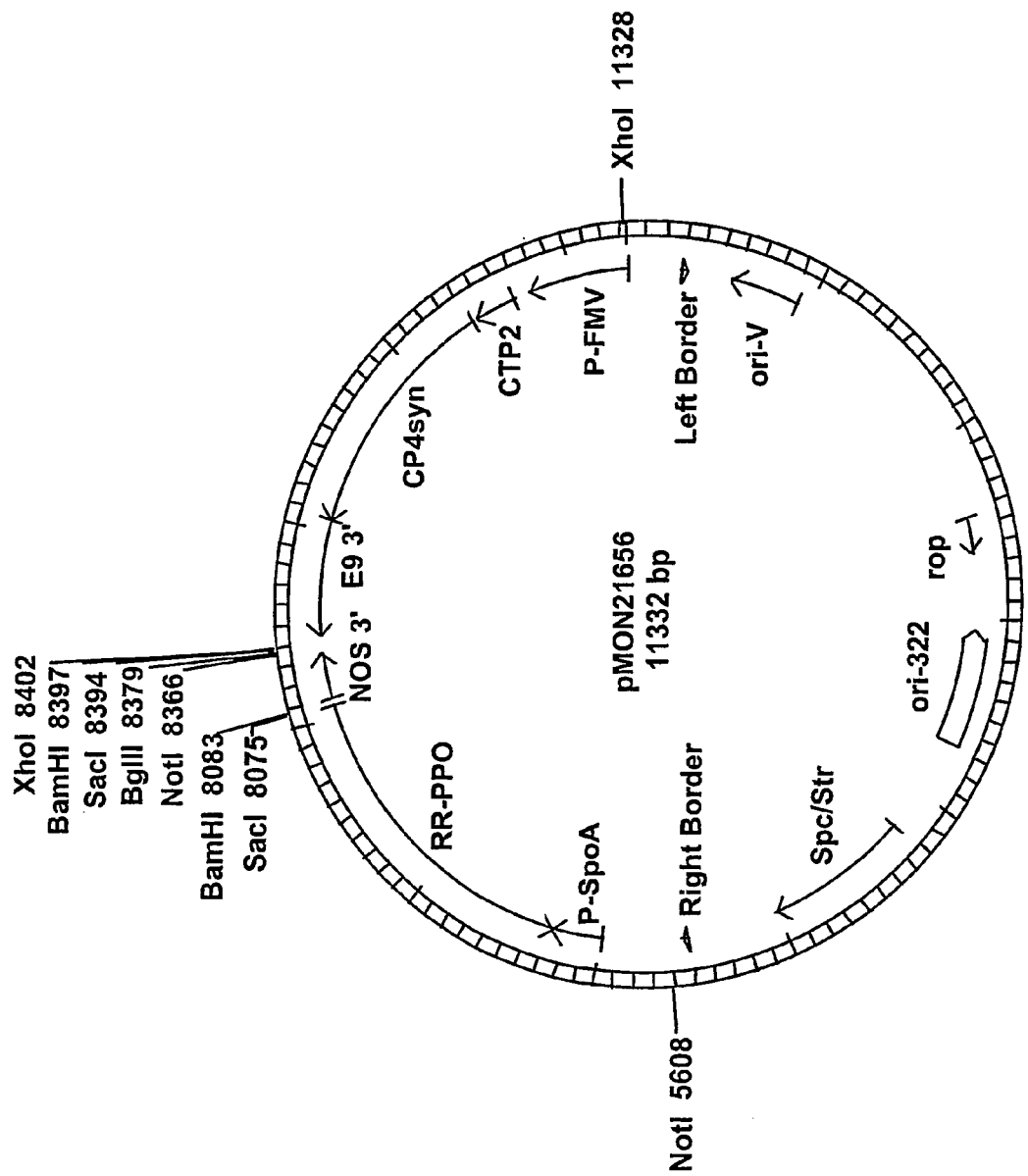
FIG. 3 shows a plasmid map for representation of pMON 21656.
Figure 4:
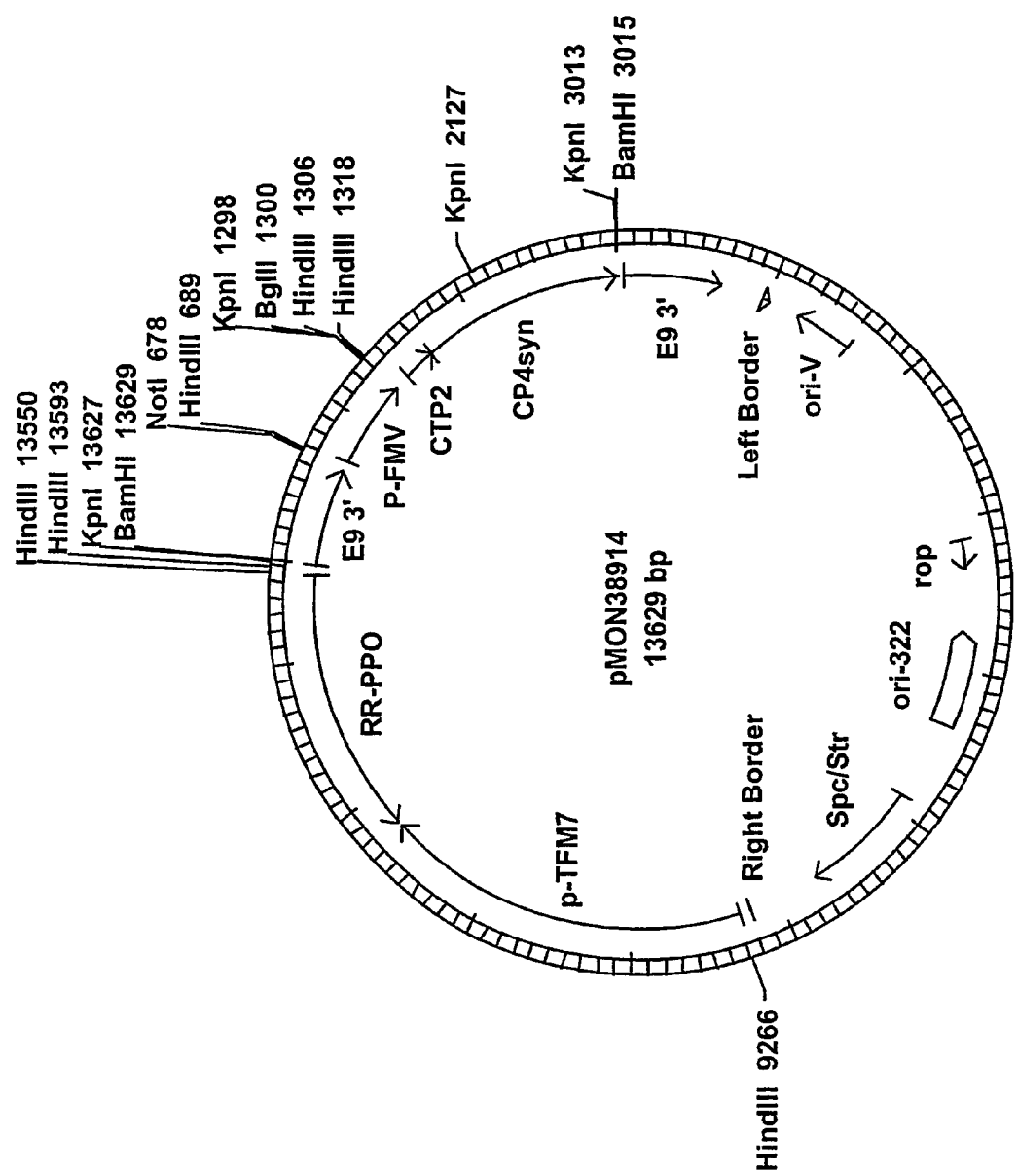
FIG. 4 shows a plasmid map for representation of pMON 38914.

1. SEQ ID NO:1 represents the sequence of a polyphenol oxidase DNA sequence cloned from potato tuber tissues of the Ranger Russet variety of *Solanum tuberosum*.
2. SEQ ID NO:2 represents the antisense sequence of a polyphenol oxidase DNA sequence cloned from potato tuber tissues of the Ranger Russet variety of *Solanum tuberosum*.
3. SEQ ID NO:3 shows a predicted amino acid sequence of the polyphenol oxidase DNA sequence as shown in SEQ ID NO:1 cloned from potato tuber tissues of the Ranger Russet variety of *Solanum tuberosum*.

DETAILED DESCRIPTION OF THE INVENTION

Definitions

In order to provide a clear and consistent understanding of the specification and the claims, including the scope given to such terms, the following definitions are provided.

"Antisense technology" means a method to introduce into cells a RNA or single-stranded DNA molecule that is complementary to the mRNA of a target DNA sequence. This antisense molecule may work by forming a base-pair with the endogenous mRNA, preventing translation of the mRNA into protein.

"Coding sequence" means a region of continuous sequential nucleic acid triplets encoding a protein, polypeptide, or peptide sequence.

"Disease resistance" means the ability of plants to develop fewer disease symptoms following exposure to a plant pathogen than a susceptible plant that does not exhibit disease resistance. Disease resistance includes complete resistance to the disease and also varying degrees of resistance manifested as decreased symptoms, longer survival or other disease parameters, such as higher yield.

"Down regulation" means the reduction in expression or activity of an endogenous plant protein, usually an enzyme by various means, primarily by use of an introduced segment of nucleic acids.

"Encoding DNA" means chromosomal DNA, plasmid DNA, cDNA, or synthetic DNA that encodes any of the enzymes disclosed herein.

"Expression" means the combination of intracellular processes, including transcription and translation, undergone by a coding DNA sequence such as a structural gene to produce a polypeptide.

"Genome" as it applies to bacteria encompasses DNA of both the chromosome and plasmids within a bacterial host cell. Encoding DNA sequences of the present invention introduced into bacterial host cells can therefore be either chromosomally integrated or plasmid-localized. The term "genome" as it applies to plant cells encompasses chromosomal DNA found within the nucleus, and organelle DNA found within subcellular components of the cell. DNA sequences of the present invention introduced into plant cells can therefore be either chromosomally integrated or organelle-localized or combinations thereof.

"Homolog" is 70% or more in sequence identity. Significant homology of a sequence very closely related to a probe sequence refers to the sequences hybridizing to the probe at 68° C. (at least 16 hours) and washed at stringent conditions (68° C., final wash with 0.1×SSC/0.1% SDS). Final wash in 2×SSC at 50° C. allows identification of sequences with about 75% homology to the probe. However, the exact relationship between stringency and sequence homology depends on base composition, the length of the probe, and the length of the homologous regions (Hames and Higgins, 1985). Preferably the hybridization conditions refer to hybridization in which the TM value is between 35° C. and 45° C. Most preferably significant homology refers to a DNA sequence that hybridizes with the reference sequence under stringent conditions.

"Hybridization" means the ability of a strand of nucleic acid to join with a complementary strand via base pairing. Hybridization occurs when complementary sequences in the two nucleic acid strands bind to one another.

"Identical" nucleotide or protein sequences are determined by using programs such as GAP or BestFit from GCG (Genetics Computer Group, Inc., Madison, Wis.) using the default parameters.

"Overexpression" means the expression of a polypeptide or protein encoded by a DNA sequence introduced into a host cell, wherein said polypeptide or protein is either not normally present in the host cell, or wherein said polypeptide or protein is present in said host cell at a higher level than without the introduced sequence during at least one part of the plant's life cycle.

"Plant" is used herein in a broad sense and means differentiated plants as well as undifferentiated plant material, such as protoplasts, plant cells, seeds, plantlets etc., that under appropriate conditions can develop into mature plants, the progeny thereof, and parts thereof such as cuttings, leaves, flowers, fruits of such plants.

"Polyadenylation signal" or "polyA signal" means a nucleic acid sequence located 3' to a coding region that promotes the addition of adenylate nucleotides to the 3' end of the transcribed mRNA from the coding region.

"Promoter" or "promoter region" means a nucleic acid sequence, usually found upstream (5') to a coding sequence, that controls expression of the coding sequence by controlling production of messenger RNA (mRNA) by providing the recognition site for RNA polymerase or other factors necessary for start of transcription at the correct site.

"Regeneration" means the process of growing a plant from a plant cell (e.g., plant protoplast or explant).

"Resistance gene" is a nucleic acid sequence encoding a protein that is directly or indirectly involved in the induction of a signal transduction pathway eventually leading to a plant defense response against any pathogen or insect, upon contact or infective exposure of the plant with that particular pathogen or insect. Resistance gene products are expressed in response to pathogen signal molecules termed elicitors.

"Selectable marker" means a nucleic acid sequence whose expression confers a phenotype facilitating identification of cells containing the selectable marker. Selectable markers include those that confer resistance to toxic chemicals (e.g., ampicillin resistance, kanamycin resistance, glyphosate resistance), complement a nutritional deficiency (e.g., uracil, histidine, leucine), or impart a visually distinguishing characteristic (e.g., color changes or fluorescence).

"Transcription" means the process of producing an RNA sequence copy from a DNA sequence template.

"Transformation" means a process of introducing an exogenous nucleic acid sequence (e.g., a vector, recombinant nucleic acid molecule) into a cell or protoplast in which that exogenous sequence is incorporated into a chromosome or is capable of autonomous replication.

"Transgenic plant" means a plant into which exogenous nucleic acid sequences are integrated.

"Vector" means any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a nucleic acid molecule in which one or more nucleic acid sequences have been linked in a functionally operative manner. Such recombinant nucleic acid constructs or vectors are capable of introducing a 5' regulatory sequence or promoter region and a selected DNA sequence into a cell in such a manner that the DNA sequence may be transcribed into a functional mRNA, which may subsequently be translated into a polypeptide or protein. Recombinant nucleic acid constructs or recombinant vectors may be constructed to be capable of expressing antisense RNAs, in order to inhibit translation of a specific RNA of interest.

Methods to Reduce Expression

Reduced expression of an endogenous gene in plants is achievable by a variety of means, including expression of an antisense sequence as disclosed in U.S. Pat. No. 5,107,065, incorporated in its entirety, herein by reference. An antisense sequence is derived from the complete (full length) coding sequence of the gene or a fragment thereof. An antisense sequence may also be a nontranslated portion of an endogenous plant gene, such as an intron, a 5' nontranslated leader region or a 3' untranslated terminator or polyadenylation region of the gene as it exists in plants. Expression of a transgenic antisense sequence allows for the down-regulation of the specific endogenous plant gene. Antisense regulation involves an antisense RNA sequence introduced into the cell, preferably under control of a strong promoter. The plant expression vector contains the appropriate leader, termination, and processing sequences for expression of an RNA transcript in transgenic plants. The transgene antisense RNA sequence interacts with the endogenous sense mRNA to affect the transcription, processing, transport, turnover, and/or translation of the endogenous sense mRNA. Antisense inhibition was first reported in electroporation of carrot protoplasts with antisense and sense constructs containing the CAT reporter gene resulted in varying inhibition of CAT activity dependent on promoter strength (Ecker et al., *Proc. Natl. Acad. Sci. U.S.A.* 83: 5372–5376, 1986). A stable inheritable antisense effect was first reported in tobacco using the NOS transgene (Rothstein et al., *Proc. Natl. Acad. Sci. U.S.A.* 84: 8439–8943, 1987). Constitutive expression of antisense chalcone synthase (CHS) in transgenic tobacco and petunia plants decreased endogenous CHS RNA and protein activity demonstrating the application of this technology in regulating endogenous gene expression (van der Krol et al., *Nature* 333: 866–869, 1988; van der Krol et al., *Plant Molecular Biology* 14: 457–466, 1990). The technology is extended to show seed specific modulation of gene expression (versus leaf-specific modulation) using the B-conglycinin promoter to drive antisense expression of GUS mRNAs in transgenic tobacco (Fujiwara et al., *Plant Mol. Biol.* 20: 1059–1069, 1992). The potential commercial value of antisense technology was first realized when transgenic tomato plants expressing antisense polygalacturonase (PG, an enzyme which partially solublizes cell wall pectin) showed a delay in fruit ripening (Smith et al., *Nature* 334: 724–726, 1988). Antisense technology has since been used to alter the expression of many plant genes, including ribulose bisphosphate carboxylase oxygenase in tobacco (Rodermel et al., *Cell* 55: 673–681, 1988), granule-bound starch synthase in potato (Visser et al., *Mol. Gen. Genet.* 225: 289–296, 1991), a photosystem II polypeptide in potato (Stockhaus et al., *EMBO J.* 9: 3013–3021, 1990), and TOM5 in tomato (Bird et al., *Biotechnol.* 9: 635–639, 1991), and PPO as described above.

Antisense sequence expression in plants has also been useful to alter plant development via the regulation of plant hormone biosynthetic pathways and relative hormone levels. For example, expression of antisense ACC synthase and ACC oxidase RNA have been shown to inhibit fruit ripening in transgenic tomato (Oeller et al., *Science* 254: 437–439, 1991; Hamilton et al., *Nature* 346: 284–287, 1990), and cantaloupe (Ayub et al., *Nature Biotechnol.* 14: 862–866, 1996). Expression of an antisense 7 transmembrane domain (7TM) receptor homologue (GCR1) RNA reduced sensitivity to cytokinins in roots and shoots of transgenic *Arabidopsis* (Plakidou-Dymock et al., *Current Biol.* 8: 315–324, 1998). Expression of antisense prosystemin severely depressed systemic wound inducibility proteinase inhibitor synthesis in transgenic tomato and decreased resistance against insects (Schaller et al., *Bioessays* 18: 27–33, 1996). Expression of antisense catalase RNAs accumulated high levels of PR-1 proteins and showed enhanced resistance to tobacco mosaic virus (Takahashi et al., *Plant J.* 11: 993–1005,1997) in transgenic tobacco. Thus, much success has been achieved using antisense technology to regulate biosynthetic pathways and hormone levels in plants. In this way, reduction in endogenous PPO levels is induced by constitutive or by the tissue-specific antisense inhibition of expression of the endogenous PPO mRNA molecule.

Another way of reducing PPO levels and thereby reducing disease susceptibility is through homology-dependent gene silencing (cosuppression) of PPO genes. Specifically, overexpression of PPO mRNA can be used to decrease PPO levels. Cosuppression, also known as cosense suppression, homology-dependent gene silencing, repeat-induced gene silencing, et cetera, is the inactivation of a gene in a cell where it is normally functional (for reviews see Baulcombe et al., *Current Opinion Biotechnol.* 7: 173–180, 1996; Meyer et al., *Annu. Rev. Plant Physiol. Plant Mol. Biol.* 47: 23–48, 1996; Matzke et al., *Plant Physiol.* 107: 679–685, 1995). A description of cosuppression in plants may be found in U.S. Patents 5,034,323, 5,231,020, and 5,283,184, all incorporated in their entirety herein by reference. Transgene induced cosuppression in plants has been shown to have useful effects which include reduced impact of viral infection, fruit ripening, affecting flower color, inactivation of infecting transposons and retrotransposons, and editing aberrant RNA transcripts (Smyth et al., *Current Biol.* 7: 793–795, 1997; Napoli et al., *Plant Cell* 2: 279–289, 1990). Many examples of cosuppression have been reported in the literature: sense suppression of caffeic acid O-methyltransferase resulted in altered stem coloration of aspen (Tsai et al., *Plant Physiology* 117: 101–112, 1998); cosuppression of a lipoxygenase isozyme (LOX2) resulted in transgenic *Arabidopsis* plants unable to accumulate jasmonic acid following wounding (Bell et al., *Proc. Natl. Acad. Sci. U.S.A.* 92: 8675–8679, 1995); cosuppression of phytochrome-regulated chlorophyll α/β 140 RNA levels in *Arabidopsis* (Brussian et al., *Plant Cell* 5: 667–677, 1993); cosuppression of a pea cDNA encoding light-activated chloroplast NADP-malate dehydrogenase in transgenic tobacco (Faske et al., *Plant Physiol.* 115: 705–715, 1997); cosuppression of *Flaveria bidentis* NADP-MDH via heterologous sorghum NADP-MDH cDNA despite only about 71% sequence homology (Trevanion et al., *Plant Physiol.* 113: 1153–1163, 1997); cosuppression of a proline-rich glycoprotein (TTS) involved in pollen tube growth in transgenic tobacco (Cheung et al., *Cell* 82: 383–393, 1995); cosuppression of phenylalanine ammonia-lyase (PAL) in transgenic tobacco (Elkind et al., *Proc. Natl. Acad. Sci. U.S.A.* 87: 9057–9061); and cosuppression of two MADS box floral binding protein genes (FBP7 and FBP11) in petunia (Colombo et al., *Plant Cell* 9: 703–715, 1997). Cosuppression of a gene or sequence for PPO expression will provide the same result as antisense regulation of these same PPO sequences or genes.

The present invention provides methods for reducing PPO expression and antisense oligonucleotides and polynucleotides complementary to any DNA sequence encoding PPO in potato plants. Such antisense oligonucleotides should be at least about six nucleotides in length to provide minimal specificity of hybridization, and may be complementary to one strand of DNA or to mRNA encoding PPO (or to a portion thereof), or to flanking sequences in genomic DNA which are involved in regulating PPO expression. The antisense polynucleotides may be as large as many nucleotides, and may extend in length up to and beyond the full coding sequence for which it is antisense. The oligonucleotides and polynucleotides can either be DNA or RNA. These antisense nucleotides may also be of chimerical source, single- or double-stranded. These nucleotides may also be prepared artificially by chemical synthesis. The action of the antisense nucleotide may result in specific alteration and/or primarily inhibition, of PPO gene expression in potato cells, as discussed above. Although one method of successful alteration of PPO gene expression will be achieved by introducing a full length cDNA clone gene in an antisense orientation, introduction of partial sequences targeted to specific regions of the sequences can be effective as well.

With antisense and co suppression methods, reduced expression levels may be achieved but with a low efficiency in transformation events. Near complete target gene suppression may occur in as few as five to ten percent of the transgenic events. Experience has shown it to occur for the PPO gene using antisense technology in about five percent of the events. A more recent development in gene suppression is a new method which results in a higher efficiency of transformation, that is, higher numbers of events with high levels of suppression from each course of transformation. This method uses a transgene which is composed of inverted repeat sequences derived from the target gene, intended to create double-stranded mRNA via mRNA hybridization due to self-complementarity. This double-stranded RNA method (or "dsRNA") has been previously reported for genes other than PPO (Waterhouse et at., Proc. Natl. Sci. USA, 95:13959–13964, 1998; Waterhouse et al., Plant Mol. Biol., 43:67–82, 2000). The inverted repeat sequences may represent a full or partial coding region, or any combination thereof, of the target gene, and can be fused either at 5' or 3' ends forming a head-to-head or tail-to-tail type of structure. Transgenic plant expression of the resultant inverted repeat gene fusion is under the control of a single promoter and a single transcriptional terminator, and is thereby intended to create double-stranded messenger RNA (mRNA).

For this inverted repeat approach, the example below describes in more detail the use of this efficient method of gene inactivation for PPO, in which a transgene is composed of inverted repeat sequences of the target gene (potato PPO). Transgenic plant expression of the resultant inverted repeat gene fusion is under the control of a single tuber-specific promoter and a single transcriptional terminator. This inverted repeat design is intended to create double-stranded tuber PPO mRNA. The construct design using inverted repeat sequences of the potato tuber PPO gene nearly completely inactivates potato tuber PPO gene expression (85–100% reduction in tuber PPO activity) in 87% of all transgenic events evaluated for the potato cultivar Ranger Russet. This inverted repeat transgene design is far superior to antisense technology in terms of the degree of PPO gene inactivation, as well as percentage of events in which the tuber PPO gene expression is highly inactivated.

Plant Transformation and Regeneration

Plants may be transformed by any of a variety of methods known to those skilled in the art such as by *Agrobacterium* transfection or biolistics methods. Potatoes are preferably transformed by the use of *Agrobacterium* transfection. A plasmid useful in any transformation method will preferably contain a selectable marker to aid in elimination of non-transformed plant cells. Plants transformed with one of the down-regulating sequences described above may be assayed for PPO expression levels. Levels of PPO protein can be measured using a PPO enzymatic activity assay. PPO levels which are no more than 20% of the natural level will perform best in the present invention. More preferably, such levels will be no more than 15% of the natural level. Even more preferably such levels will be no more than 5% of the natural level. The plants which are amenable to transformation and use in the present invention are many. Examples include, but are not limited to, potato, sweet potato, banana, apple, avocado, broccoli, cauliflower, lettuce, grapevine, tobacco, bean, peach, pear and apricot. Each of these plants may be transformed by one of ordinary skill in the art using known methods.

Regeneration will be conducted in obtaining a whole plant from the transformation process. The term "regeneration", means growing a whole plant from: a plant cell, a group of plant cells, or a piece of tissue. Plant parts obtained from the regenerated plant in which expression of a PPO gene has been altered, such as leaves, flowers, seeds, fruit and the like are within the definition of "plant" as stated above, and are included within the scope of the invention. Progeny and variants and mutants of the regenerated plants are also included, especially if these parts comprise the introduced DNA sequences.

Disease Control

What is described here is a new method for disease control that is based on the modification of parts of the phenylpropanoid pathway. This pathway, initiated by the deamination of phenylalanine, leads to the biosynthesis of multiple lignins, flavonoids, coumarins, benzoic acids and esters such as chlorogenic acid.

Importantly, decreased levels of chlorogenic acid were previously shown to be associated with increased susceptibility to, e.g., *P. infestans* in potato (Kening et al., 1995), *Cercospora nicotianae* in tobacco (Maher et al., *Proc. Natl. Acad. Sci., USA* 91: 7802–7806, 1994), and *Monilinia fructicola* in peach (Wang et al., *Phytopathology* 87: S101, 1997; Bostock et al., *Phytopathology* 87: S101, 1997). Chlorogenic acid or other phenylpropanoid products may also provide either a direct antifungal activity or limit pathogen-induced oxidative stress through their antioxidant, iron-chelating or protease inhibitor-binding activities (Yamasaki and Grace, FEBS Lett., 1998, Feb. 6, 422(3): 377–380, 1998; Yoshino and Murakami, Anal Biochem. March 1, 257 (1): 4044, 1998; Felton et al., *J. Insect Physiol.* 35: 981–990, 1989).

The in vivo concentrations of free phenolics such as chlorogenic acid are, in part, dependent on the activity of PPO which catalyzes the oxidation of chlorogenic acid and other phenolics to quinones upon wound-induced release from chloroplasts. It has been proposed that low PPO levels may trigger expression of phenylalanine ammonia lyase (PAL), the rate-limiting enzyme in the biosynthesis of phenolics such as chlorogenic acid (Mayer et al., *Annu. Rev. Plant Physiol. Plant Mol. Biol.* 47: 23–48, 1996; Smith and Rubery, Planta 151, 535–540, 1981).

As compared to the PPO levels found in above-ground parts of plants, there is no apparent role for the up to 30-fold higher PPO levels in potato tubers (Thygesen et al., *Plant Physiol.*, 109: 525–531, 1995). In fact, these high concentrations of PPO lead to a rapid enzymatic browning upon wounding which can greatly reduce the agronomic value of potato tubers.

The present invention surprisingly demonstrates that plants can be made to demonstrate resistance to the highly virulent US-8 genotype of *P. infestans* through genetic engineering. One possible mode of this accomplishment may be that decreased concentrations of PPO result in an increased accumulation of free phenolics such as chlorogenic acid and, subsequently, trigger enhanced disease resistance against a variety of fungal pathogens.

Promoters

In order for a newly inserted gene or DNA sequence, in the case of antisense DNA, to be transcribed, resulting in an antisense RNA molecule, preferably proper regulatory signals should be present in the proper location with respect to the coding or antisense sequence. These regulatory signals may include a promoter region, a 5' non-translated leader sequence and a 3' polyadenylation sequence as well as enhancers and other known regulatory sequences. The promoter is a DNA sequence that directs the cellular machinery to transcribe the DNA to produce RNA. Promoters useful in the present invention include those that confer appropriate cellular and temporal specificity of expression. Such promoters include those that are constitutive or inducible, environmentally- or developmentally-regulated, or organelle-, cell-, or tissue-specific.

Promoters which are useful in the present invention are those which will initiate transcription in tissues in which polyphenol oxidase is produced. Examples of such tissues include tuber tissues, fruit tissues, seed tissues, root tissues, flower tissues, and leaf tissues. Examples of promoters useful in the present invention include, but are not limited to promoters for granule bound starch synthases, soluble starch synthases, ADP glucose pyrophosphorylases, sucrose synthases, starch branching enzymes, starch debranching enzymes, polyphenol oxidases, sporamin proteins, and patatin proteins (Class I). Examples of tuber-specific promoters useful in the present invention include the granule-bound starch synthase (GBSS) promoter from potato, the SporaminA promoter from sweet potato (Ohta et al., Mol Gen Genet. 225:369–378, 1991), the TFM7 tomato fruit-specific promoter (Santino et al., Plant Mol Biol, 33:405–416, 1997), and the ADP-glucose pyrophosphorylase small subunit (smADPGPP) promoter from potato (Nakata and Okita, Mol Gen Genet, 250:581–592, 1996). Examples of constitutive promoters useful in the present invention include the e35S promoter from the Cauliflower Mosaic Virus (CaMV promoter) (Odell et al. (1985) *Nature* 313: 810), and the $^{35}$S promoter from the Figwort Mosaic Virus (FMV promoter) (Richins et al. (1987) NAR 20: 8451). These two are distantly related *caulimovirus* promoters and are among the strongest promoters commonly used in plant transformation.

Polyadenylation Signal

The 3, non-translated region of the chimeric plant gene contains a polyadenylation signal which functions in plants to cause the addition of polyadenylate nucleotides to the 3' end of the RNA. Examples of suitable 3' regions are the 3' transcribed, non-translated regions containing the polyadenylated signal of *Agrobacterium* the tumor-inducing (Ti) plasmid genes, such as the nopaline synthase (NOS) gene, and plant genes like the 3' non-translated region of the pea rbcS-E9 gene.

Polyphenol Oxidase DNA Sequence Sources

The PPO sequence used in the DNA constructs for plant transformation in the present invention may be any PPO DNA sequence. It is not limited to the potato tuber PPO sequence for the isoform product, although it is preferred for potato tuber-specific inhibition of PPO. Genomic or cDNA PPO sequences from other plant sources and/or from other non-tuber tissues may be moved into plasmids containing plant-appropriate regulatory sequences and used in the present invention. Any PPO sequence that comprises any portion of its open reading frame, or any portion of its 5' or 3' untranslated region, or any combination of portions or the entirety of its open reading flame plus portions or the entirety of its untranslated regions, may be moved into plasmids containing plant-appropriate regulatory sequences and used in the present invention.

A PPO cDNA sequence (PPO-P1) for a potato leaf isoform polyphenol oxidase has been previously identified in which the gene source was the Katahdin cultivar (Hunt, M. D., et al., 1993, *Plant Mol. Biol.* 21:59–68). Additionally, the gene for the tuber predominant plus tuber-specific PPO isoform was cloned from the Ranger Russet potato cultivar, based upon expression analysis of the various potato PPO isoforms, specifically of the major tuber isoform POT32 (Thygesen, P. W., et al., 1995, Plant Physiol. 109:525–531). Using the GenBank sequence (accession U22921) for POT32, specific primers were made and the gene was amplified by PCR from Ranger Russet genomic DNA. Sequencing of the entire open-reading-frame of the PCR gene product revealed that the sequence from the Ranger Russet cultivar is 98% identical to the published POT32 gene which is from the Norchip cultivar. Thus, the putative tuber-predominant, putative tuber-specific Ranger Russet PPO, referred to hereafter as the "Ranger Russet tuber PPO sequence" or "RR-PPO sequence," was chosen to be used in the examples below.

Transgenic potato tubers containing less than 20% of wild-type PPO levels display enhanced resistance against *P. infestans*. It will be recognized by one skilled in the art that these tubers will also display enhanced disease resistance against certain other fungal pathogens that infect potato tubers. Furthermore, the experiments detailed below suggest that suppression of PPO may result in the control of fungal pathogens of potatoes including, but not limited to, *Spongospora* (powdery scab), *Rhizoctonia* (black scurf), *Fusarium* (dry rot), *Verticillium* (*Verticillium* wilt), *Alternaria* (early blight), *Polyscytalum* (skin spot), *Sclerotium* (white mold), *Rosellinia* (black rot), *Helicobasidium* (violet root rot), *Macrophomina* (charcoal rot), and *Helminthosporium* (silver scurf). The methods may also result in control of fungal pathogens including, but not limited to, *Phytophthora, Cercospora* and *Monilinia*, on other plants.

After a general description of the present invention, the following specific examples are presented to further depict the same in a specific manner. These examples are provided by way of illustration, and are not in any way intended to limit the present invention. Therefore, these examples can not be construed as to limit the scope of the invention.

EXAMPLES

Example 1

Construction of Antisense Plant Vectors

In order to obtain tuber-specific expression of the potato leaf cDNA, a plant expression vector, pMON21624, which contained the PPO-P1 sequence was constructed as follows: The PPO-P1 sequence was isolated from a potato leaf cDNA library as a SacI-BglII fragment, and fused in antisense orientation to the 3' end of the e35S promoter and 5' end of the E9 3' nontranslated polyadenylation region by ligation into a SacI-BglII sites of a double-bordered binary Ti plasmid vector. The vector contained the e35S/NPTII/NOS 3' selectable marker cassette, which confers plant resistance to kanamycin. From the resultant plasmid, pMON21621, the e35S promoter was removed as a HinDIII-BglII fragment and replaced with the potato GBSS promoter via ligation as a HinDIII-BglII fragment to produce pMON21622, which contains the GBSS/antisense PPO-P1/E9, 3' cassette. The e35S/NPTII/NOS 3' cassette was then excised as a NotI-XhoI fragment from pMON21622. The FMV/CTP2-CP4/E9 3' selectable marker cassette which confers plant tolerance to glyphosate (Padgette et al., Herbicide Res. Crop: Agricultural, Environmental, Economic, Regulatory and Technical Aspects, CRC Press, 53–84, 1996), was isolated as a NotI-SalI fragment from pMON17314, which is a pUC-based *Escherichia coli* cloning vector, and ligated into the NotI-XhoI sites of pMON21622 to produce the final plasmid, pMON21624.

The RR-PPO sequence, which was amplified by PCR from Ranger Russet genomic DNA, was cloned into the HindIII site of pMON38201, which is a pBluescriptII-SK(−) (Stratagene)-based cloning vector with a modified multicloning polylinker. The resultant vector, pMON21646, served as the RR-PPO sequence source for all subsequent plant vector constructions. In order to obtain tuber-specific expression of the tuber PPO sequence, three different plant expression vectors which contained the RR-PPO sequence were constructed.

The first expression vector, pMON21652, was built as follows: The RR-PPO sequence was isolated as a SalI-BamHI fragment from pMON21646, while the E9 3' non-translated polyadenylation fragment was isolated from pMON21647 (not described herein) as an XhoI-NotI fragment. pMON17269 is a double-bordered binary Ti plasmid vector which contains the smADPGPP promoter, plus the e35S/NPTII/NOS 3' selectable marker cassette. In order to fuse the smADPGPP promoter to the RR-PPO sequence in antisense orientation, pMON17269 was digested with BglII and NotI. In a triple ligation, the BamHI site at the 3' end of the RR-PPO sequence was ligated to the BglII site at the 3' end of the smADPGPP promoter, the SalI site of the RR-PPO sequence was ligated to the XhoI site at the 5' end of the E9 3' fragment, and the NotI site of the E9 3' fragment was ligated with the NotI site of pMON17269. The resultant plasmid, pMON21650, containing the smADPGPP/antisense RR-PPO/E9 3' cassette, was then digested with NotI-XhoI in order to excise the e35S/NPTII/NOS 3' cassette. The FMV/CTP2-CP4/E9 3' selectable marker cassette was isolated as a NotI-SalI fragment from pMON17314, which is a pUC-based *E. coli* cloning vector, and ligated into the NotI-XhoI sites of pMON21650 to give the plasmid, pMON21652.

The second expression vector, pMON21656, was constructed as follows: pMON31813 is a cloning vector which contains the SpoA promoter/polylinker/NOS3' cassette flanked by NotI sites. The RR-PPO sequence was isolated from pMON21646 as a SacI-BamHI fragment and ligated in antisense orientation into the BglII-SacI sites of pMON31813 producing pMON21655. pMON34018 is a double-bordered binary Ti plasmid vector which contains the FMV/CTP2-CP4/E9 3' selectable marker cassette. The SpoA/antisense RR-PPO/NOS 3' cassette was excised from pMON21655 as a NotI fragment, and ligated into the unique, dephosphorylated NotI site of pMON34018, to produce the plasmid, pMON21656.

The third expression vector, pMON38914, was constructed as follows: The RR-PPO sequence was isolated from pMON21646 as a KpnI-BamHI fragment, while the TFM7 promoter was isolated from tomato library as a HinDIII-BglII fragment. pMON10097, which is a double-bordered binary Ti plasmid vector which contains the E9 3' nontranslated polyadenylation fragment between the borders, was digested with KpnI and HinDIII. In a triple ligation, the BamHI site at the 3' end of the RR-PPO gene was ligated to the BglII site at the 3' end of the TFM7 promoter, the KpnI site of the RR-PPO gene was ligated to the KpnI site at the 5' end of the E9 3' fragment, and the HinDIII site of the TFM7 promoter fragment was ligated with the HinDIII site of pMON10097. The resultant plasmid, pMON21651, contained the TFM7/antisense RR-PPO/E9 3' cassette and was digested with NotI-XhoI. The FMV/CTP2-CP4/E9 3' selectable marker cassette was isolated as a NotI-SalI fragment from pMON17314, which is a pUC-based *E. coli* cloning vector, and ligated into the NotI-XhoI sites of pMON21651 to produce the plasmid, pMON38914.

Example 2

Transformation, Expression and Regeneration of Potato

The constructs pMON21624, pMON21652, pMON21656, and pMON38914 were independently mobilized into disarmed ABI *Agrobacterium tumefaciens* strain by electroporation using a Bethesda Research Laboratories Cell-Porator according to the manufacturer's recommended protocol. Electroporated cells were allowed to recover in LB broth with shaking (200 rpm) at 30° C. for 2 hours. Transformed *A. tumefaciens* cells were selected by plating out the electroporated cells on LB agar containing 25 ug/ml chloramphenicol, 50 ug/ml kanamycin, and 75 ug/ml spectinomycin.

Russet Burbank and Ranger Russet potato cultivars underwent *Agrobacterium*-mediated transformation using a glyphosate selection transformation protocol as described in U.S. Pat. No. 4,970,168, incorporated in its entirety herein by reference. Russet Burbank cultivar was transformed with only pMON21624, while Ranger Russet cultivar was independently transformed with pMON21652, pMON21656, and pMON38914.

Specifically, sterile shoot cultures of each of the cultivars were maintained in vials containing 10 ml of PM medium (Murashige and Skoog (MS) inorganic salts, 30 g/l sucrose, 0.17 g/l Na H$_2$PO$_4$H$_2$O, 0.4 mg/l thiamine-HCl, and 100 mg/l myo-inositol, solidified with 2 g/l Gelrite at pH 6.0). When shoots reached approximately 5 cm in length, stem internode segments of 7–10 mm were excised and inoculated for 15 min in a square petri dish, with an *Agrobacterium tumefaciens* overnight liquid culture diluted to an optical density of 0.2–0.33. The stem explants were co-cultured for three days at 23° C. on a sterile filter paper placed over 1.5 ml of a tobacco cell feeder layer overlaid on ⅒ P medium (⅒ strength MS inorganic salts and organic addenda without casein as in Jarret, et al. (1980), 30 g/l sucrose and 8.0 g/l agar). About 50 explants were placed per co-culture plate. Following co-culture, the explants were transferred to full strength P-1 medium for callus induction, composed of MS inorganic salts, organic additions as in Jarret, et al. (1980) with the exception of casein, 10 mg/l AgNO$_3$, 5.0 mg/l Zeatin Riboside, and 0.1 mg/l naphthaleneacetic acid (NAA) (Jarret, et al., 1980), for 2 days. Carbenicillin (500 mg/l) is included to inhibit bacterial growth. Explants were subsequently transferred onto callus induction media which contained glyphosate (0.025 mM) to select for transformed cells. After four weeks the explants were transferred to shoot induction media of the same composition but with 0.3 mg/l gibberellic acid (GA3) replacing NAA (Jarret, et al., 1981) to promote shoot formation. Explants were transferred to fresh shoot induction media every 4 weeks for 12 weeks. Shoots begin to develop approximately two weeks after transfer to shoot induction medium; these were excised and transferred to vials of P medium for rooting every 4 weeks for 12 weeks.

Example 3

Oxidative Browning Assay and Catechol Assay for PPO Activity in Potato Tubers

Transgenic Russet Burbank and Ranger Russet lines were initially screened for tuber PPO activity using greenhouse-grown mini-tubers; Transgenic plantlets with sufficient root development in tissue culture were transplanted to soil which consisted of 2 parts Metro-350, 1 part fine sand, 1 part Ready-Earth in 12 inch wide pots. The plantlets were grown in a greenhouse in which conditions throughout a 4–5 month growth period included a 15 hr photoperiod, 40–60% relative humidity, fertilization with Peter's Special 20–20–20, and 24-27° C. day/13–16° C. night incubation. At 2.5 months, fertilization was stopped, and upon senescence, tubers were harvested and stored at 4° C. until evaluation.

Mature greenhouse mini-tubers, as well as field-grown tubers were measured for PPO activity first by an Oxidative Browning Assay and then by a Catechol Assay. The Oxidative Browning Assay of tuber homogenates relies only upon endogenous tuber phenolic compounds as substrates for PPO. With this assay, no additional substrate is added to the tuber homogenates, and the natural browning color is allowed to develop over 20 hours. The Catechol Assay of tuber homogenates involves addition of catechol (DOPA substrate analog) to the extract, followed by monitoring the rapid increase in color development spectrophotometrically. The majority of lines with wild type tuber PPO activity levels were eliminated by the Oxidative Browning Assay; therefore, the Catechol Assay was performed as a more stringent confirmation assay on transgenic lines initially identified as having low PPO activity by the Oxidative Browning Assay.

1. PPO-Oxidative Browning Assay Of Tuber Homogenates. For each transgenic line, measurements were performed on samples of tuber tissue (approximately 1–5 grams) extracted by a #8 cork punch from the center of each tuber. Tuber tissue was homogenized using a Polytron (Kinematica Polytron, Taiwan) on speed five for approximately 30 seconds, in 20 mM sodium acetate buffer, pH 5.2, at a 1:5 (w:v) tissue to buffer ratio. Proteins (usually 5 µL) were analyzed in duplicate by Bradford assay. The homogenate was allowed to oxidize at 22° C. for 20 hours in the same round bottom tube, centrifuged at 12,000 rpm for 5 minutes, and decanted for optical density measurements. Optical density was directly measured at 475 nm. Units of oxidative browning rate were calculated as optical density after 20 hours divided by mg of protein on a per ml basis (divided by mg protein/mL). In the case of greenhouse mini-tubers, tyrosine was optionally added to the homogenates immediately after homogenization at a final concentration of 2.0 mM in order to intensify the brown color development after 20 hours.

2. PPO-Catechol Assay of Tuber Homogenates. For each transgenic line, measurements were performed on samples of tuber tissue (approximately 1–5 grams) extracted by a #8 cork punch from the center of each tuber. Tuber tissue was homogenized using a Polytron on speed five for approximately 30 seconds, in 20 mM sodium acetate buffer, pH 5.2, at a 1:5 (w:v) tissue to buffer ratio, and centrifuged at 12,000 rpm for 3 min. Extracted samples were desalted in duplicate (175 μL each) using Boehringer Mannhein Protein Quick-Spin desalting columns equilibrated with 20 mM sodium acetate buffer, and assayed in duplicate for PPO activity using 10 mM final concentration catechol as substrate. Protein was measured in duplicate on 10 μL the desalted samples by Bradford assay. One ml of the PPO reaction mixture contained 100 μL of 100 mM catechol, 100 μg of total extracted protein (usually 50–100 μL of desalted extract), and a volume of 20 mM sodium acetate buffer, pH 5.2 (usually 800–850 μL) to bring total reaction volume to 1.0 mL. The mixture was rapidly mixed and the change in optical density was monitored at 420 nm for the first 2 minutes. PPO specific activity was calculated as the change in OD at 420 nm/min/mg protein assayed.

Example 4

Bruise Barrel Assay for Black Spot Bruise Resistance

Transgenic Ranger Russet lines which demonstrated greater than a 50% reduction in tuber PPO activity via Catechol Assay of greenhouse mini-tubers, were evaluated for black spot bruise resistance in field grown tubers. Anti-black spot bruise field trials were conducted twice in two consecutive years at Parma, Id., Notus, Id., Hancock, Wis., and Hermiston, Oreg. The trials consisted of either tissue culture propagated plantlets, or first generation certified tuber seed. All trials consisted of 3 to 6 repetitions of 12 to 20 plants/seed pieces per repetition per transgenic line, with a complete randomized block design. Tubers in the 6 to 12 ounce category were harvested at full maturity from all repetitions, and subsequently underwent a Bruise Barrel Assay for black spot bruise susceptibility. The Bruise Barrel Assay mimics commercial conditions of physical impact encountered during harvest, shipping, and storage of potato tubers, thereby allowing identification of transgenic lines with resistance to black spot bruise.

Bruise Barrel Assay. Field collected tubers were handled with care to prevent bruising, and were allowed to warm to 22° C. for 24 hours. Fifteen tubers per field repetition were placed in a motor-driven bruise barrel apparatus, and the barrel was turned on and allowed to rotate for exactly 15 revolutions. The barrel was equipped with a counter set for 15 revolutions in order to always stop the barrel exactly in the same position. Tubers were removed from the barrel and placed in a bucket, with each bucket representing a single field repetition consisting of 15 tubers. The tubers were held at 22° C. for 7 days to allow black spot bruises to develop, at which point a Hobart peeler was employed to partially peel each repetition of 15 tubers. This process was referred to as an Abrasive Peel in which the Hobart peeler was run for exactly 30 seconds with running water supplied. Tubers were removed and hand-peeled to complete the peeling process. All black spot bruises were immediately counted per tuber, taking care to not include shatter bruises, in order to obtain a total count per 15 tubers. For each repetition, all 15 peeled tubers were returned to the same bucket and held at 22° C. for 24 hours. Tubers were removed from the buckets and individually assigned an Abrasive Peel Rating, based on the propensity of the entire tuber tissue to darken or discolor. Abrasive Peel ratings were based on the following visual color scale: 1=white or light yellow; 2=small areas of light gray; 3=more or larger areas of light gray; 4=large areas of intense graying, darkening, or blackening; 5=tuber blackened completely.

Three different variations of the Bruise Barrel Assay were employed. Bruise Barrel Assay 1 (BBA1) involved bruising groups of 15 tubers (usually three or more repetitions of 15 tubers per line) immediately after harvest. The tubers were then allowed to sit at 22° C. for 7 days, followed by peeling and counting of black spot bruises. Bruise Barrel Assay 2 (BBA2) involved bruising the same number and repetitions of tubers immediately after harvest. However, the tubers were stored at 4° C. for 4 months, after which they were removed from cold storage and peeled to count black spot bruises. Bruise Barrel Assay 3 (BBA3) involved storing the same number and repetitions of tubers first for 4 months at 4° C., after which the tubers were removed from cold storage, bruised, allowed to sit at 22° C. for 7 days, and then peeled to count black spot bruises.

Example 5

Analysis of Russet Burbank Potato Line

The transformation of Russet Burbank with pMON21624 generated six lines, designated Marie and RBHS90 lines, which demonstrated a significant reduction in greenhouse mini-tuber PPO activity levels from that of nontransgenic Russet Burbank control (Table 1). These six Russet Burbank lines were grown at a certified seed facility in Islands Falls, Me., in order to obtain disease-free field tubers to test in late blight resistance studies, as well as to measure for field tuber PPO activity levels.

For each of the six transgenic Russet Burbank lines plus Russet Burbank control, six tubers in the 6–8 ounce category per line were obtained from the same plots in Island Falls, Me., in which samples were taken for tuber PPO activity assay. To prepare the late blight tuber inoculum, $P.$ $infestans$ isolate A2 US8 was grown for 10 days at 18° C. on petri plates containing rye agar-A. Sterile distilled water suspensions of sporangia from 40 plates were pooled and placed in a single Erlenmeyer flask and incubated at 8° C. for 3 hours to induce zoospore formation. The concentration of zoospores was determined with a hemacytometer and the suspension was diluted to approximately $2 \times 10^4$ zoospores/ml. This diluted suspension also contained approximately 1000 sporangia/ml. All six tubers for each line were placed in 7-Way trays, which provided optimum conditions for washing, drying, inoculating, and incubation of the tubers. Each tray held 6 tubers, and the tubers were washed with tap water. When dry, the tubers were each wounded with a circular Flour Peg steel comb, 1 inch diameter, which contained approximately 60 steel needle-like teeth. The comb was pricked once through the skin of the tuber at its longitudinal center, and the zoospore suspension was evenly sprayed onto the wounded tubers with an atomizer. Immediately after inoculation, the trays were incubated in a mist chamber at 17° C., 100% relative humidity for 24 hours, and then at 20° C., 80–90% relative humidity for 12 days. Following incubation, the tubers were carefully peeled completely by hand and were rated for disease severity of the tuber tissue. The results in Table 1 indicate a direct correlation between the reduction in field tuber PPO activity levels, and a reduction in the percentage of disease severity area as well as reduction in the spread of disease into the tubers, as compared to the control.

Transgenic tubers of lines MARIE-65, HS90–22 and HS90–25, which contained>20% of wild-type PPO levels were equally susceptible to *P. infestans* as controls, with at least 54% and 71% of the tuber surface displaying disease symptoms at the day 12- and day 20-time points, respectively. Importantly, tubers of transgenic lines MARIE-72, HS90-23 and HS90-07, with PPO levels below 20% of the levels in untransformed plants, displayed a significantly enhanced level of disease resistance. Twelve days post-infection, disease symptoms were, on average, reduced with 36% in transgenic tubers derived from these 'low PPO' plants compared to untransformed control tubers. Eight days later, 'low PPO' tubers still displayed 28% less disease symptoms than the potato lines containing higher concentrations of PPO. To confirm that 'low PPO' levels were correlated with reduced disease symptoms, the spread of *P. infestans*-induced disease symptoms in the tubers was measured. As shown in Table 1, the depth of affected tissue in both controls and transgenic lines containing at least 20% of wild-type PPO levels was between 4.3 and 4.8 mm, whereas disease symptoms were limited to 2.3–3.3 mm in tubers of transgenic lines with less than 20% PPO. In examining the physical appearance of the disease symptoms, transgenic 'low PPO' tubers clearly displayed less disease-induced symptoms than the Russet Burbank wild-type controls.

TABLE 1

Percent disease severity in Russet Burbank tubers inoculated with *Phytophthora infestans* isolate A2 US8, and corresponding percent reduction in tuber PPO activity for lines transformed with pMON21624.

| Line ID | % Red. in PPO Greenhouse[1] | % Red. in PPO Field[2] | % Disease severity area on tubers 12 DAI | 20 DAI | Spread of Late Blight disease in tubers (depth in mm) 12 DAI | 20 DAI |
|---|---|---|---|---|---|---|
| RB Control | 0 | 0 | 61 | 77 | 4.3 | 5.0 |
| HS90-23 | 84 | 99 | 39 | 56 | 2.3 | 3.8 |
| Marie-72 | 94 | 89 | 44 | 52 | 3.3 | 3.3 |
| HS90-07 | 87 | 86 | 38 | 58 | 3.3 | 4.5 |
| HS90-25 | 71 | 76 | 54 | 71 | 4.8 | 4.8 |
| Marie-65 | 65 | 31 | 69 | 80 | 4.8 | 4.5 |
| HS90-22 | 26 | 7 | 67 | 78 | 4.5 | 8.0 |
| LSD | | | 6.9 | 13 | 0.9 | 3.6 |

[1]= average of two mini-tubers evaluated per line.
[2]= average of 4 tubers evaluated per line. Tubers were from same source as those used for *P. infestans* isolate US8 inoculations.

Example 6

Analysis of Ranger Russet Potato Line

The transformation of Ranger Russet with pMON38914 generated six lines, designated Gemini, which demonstrated a significant reduction in greenhouse mini-tuber PPO activity levels from that of wild type Ranger Russet control (Tables 2, 3, & 4). These 6 Ranger Russet lines underwent field trial evaluations in Notus, Id., and Hancock, Wis., in which they were evaluated for black spot bruise resistance using the BBA1, and BBA2. The black spot bruise data shown in Tables 2 and 3 indicate these lines demonstrate a strong correlation in the reduction of greenhouse mini-tuber PPO activity with a significant reduction or elimination of black spot bruises in both BBA1 and BBA2 at both field trial locations. Significant reductions in Abrasive Peel ratings at both trial sites also indicated a decreased propensity for the tuber tissue to form black melanin pigment in the transgenic lines, due to the reduced activity of PPO in the tuber.

TABLE 2

Black spot bruise resistant Ranger Russet lines: Field Trials at Hancock, WI, and Notus, ID. BBA1 - Tubers bruised and evaluated at harvest. All bruise and abrasive peel data represent the average of 3 repetitions of 15 tubers per repetition.

| Line | % Red. in PPO Greenhouse[1] | Hancock, WI Mean # Bruises | Hancock, WI Abrasive Peel Rat. | Notus, ID Mean # Bruises | Notus, ID Abrasive Peel Rat. |
|---|---|---|---|---|---|
| Ranger Control | 0 | 62 | 4.6 | 28 | 3.9 |
| Gemini-087 | 98 | 0* | 2.6* | 0* | 1.7* |
| Gemini-108 | 81 | 0* | 2.7* | 0* | 1.6* |
| Gemini-180 | 73 | 0* | 2.5* | 4* | 1.9* |
| Gemini-200 | 69 | 0* | 2.4* | 0* | 1.5* |
| Gemini-157 | 20 | 44 | 4.4 | 29 | 4.0 |
| Gemini-191 | 9 | 51 | 4.5 | 34 | 4.0 |

*= Statistically different from control.
[1]= average of three mini-tubers evaluated per line.

TABLE 3

Black spot bruise resistant Ranger Russet lines: Field Trials at Hancock, WI, and Notus, ID. BBA2 - Tubers bruised at harvest, then stored 4 months at 4° C., and then peeled for evaluation. All bruise and abrasive peel data represent the average of 3 repetitions of 15 tubers per repetition.

| Line | % Red. in PPO Greenhouse[1] | Hancock, WI Mean # Bruises | Hancock, WI Abrasive Peel Rat. | Notus, ID Mean # Bruises | Notus, ID Abrasive Peel Rat. |
|---|---|---|---|---|---|
| Ranger Control | 0 | 90 | 4.3 | 22 | 4.0 |
| Gemini-087 | 98 | 0* | 3.0* | 0* | 2.4* |
| Gemini-108 | 81 | 0* | 3.3* | 0* | 2.6* |
| Gemini-180 | 73 | 0* | 3.1* | 1* | 2.5* |
| Gemini-200 | 69 | 0* | 3.0* | 1* | 2.5* |
| Gemini-157 | 20 | 86 | 4.3 | 23 | 4.4 |
| Gemini-191 | 9 | 87 | 4.2 | 18 | 4.1 |

*= Statistically different from control.
[1]= average of three mini-tubers evaluated per line.

These same six Ranger Russet Gemini lines were grown at a certified seed facility in Island Falls, Me., in order to obtain disease-free field tubers to test in late blight resistance studies, as well as to measure for field tuber PPO activity levels. Tubers obtained from all six Ranger Russet lines grown in there demonstrated that reduction of mature field tuber PPO activity correlated closely with that observed for the same lines grown in the greenhouse (Table 4). The combination of black spot bruise resistance, plus field-level reduction of tuber PPO activity level provided sample test material for evaluation of resistance to the late blight pathogen *P. infestans* isolate US8.

To confirm that strong reductions in PPO levels not only lead to a reduction of disease symptoms but also result in reduced fungal growth, a "tuber slice fungal penetration" study was designed. For each of the six transgenic Ranger Russet lines plus wild type Ranger Russet control, six tubers in the 6–8 ounce category per line were obtained from the same field plots in Island Falls, Me., in which samples were taken for tuber PPO activity assay. To prepare the late blight tuber inoculum, P. infestans isolate US8 was grown for 10 days at 18° C. on petri plates containing Rye Agar-A until the agar surface was completely covered. Tubers were cut at the center point to obtain one thick (1 cm) cross-sectional slice per tuber. Each tuber slice was placed horizontally onto a square agar plug (0.5 cm width) containing P. infestans sporangia, and incubated in a sealed petri dish (100% humidity) at 20° C. Five days post-inoculation, the top surfaces of the tuber slices were analyzed phenotypically for the presence of P. infestans that had grown through the slices and subsequently sporulated. Each slice was measured for the percentage of disease severity area across the top surface. The tissue disease severity ratings in Table 4 indicate a direct correlation between the reduction in field tuber PPO activity levels, and a reduction in the percentage of disease severity area across the upper surface of the slice. Importantly, it was also found that P. infestans sporulated vigorously on slices obtained from Russet Burbank control tubers, thereby producing significant biomass (mycelia and spores), but that tuber slices from all 'low PPO' Gemini lines contained hardly any P. infestans biomass (mycelia and spores) (data not shown).

TABLE 4

Percent disease severity on top surface of Ranger Russet cross-sectional tuber slices inoculated from the underside surface with P. infestans isolate A2 US8, and corresponding percent reduction in tuber PPO activity, for lines transformed with pMON38914.

| Line ID | % Reduction in PPO Greenhouse[1] | % Reduction in PPO Field[2] | % Disease severity area on tuber slices: 5 DAI[3] |
|---|---|---|---|
| Ranger Control | 0 | 0 | 59 |
| Gemini-087 | 98 | 99 | 27 |
| Gemini-108 | 81 | 90 | 45 |
| Gemini-180 | 73 | 86 | 45 |
| Gemini-200 | 69 | 79 | 41 |
| Gemini-157 | 20 | 49 | 30 |
| Gemini-191 | 9 | 0 | 64 |

Figure 5:
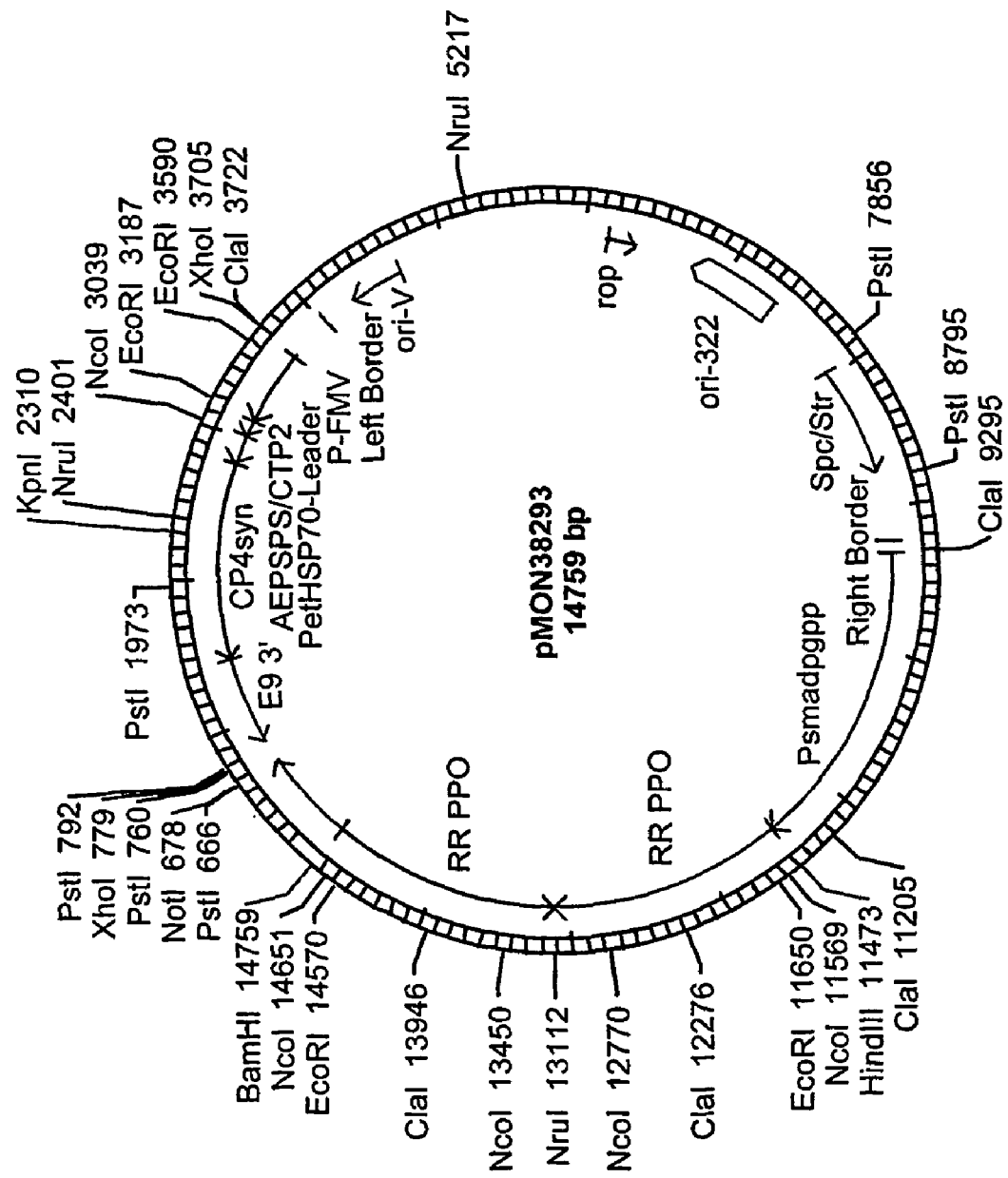
FIG. 5 shows a plasmid map for representation of pMON 38293.

[1] = average of three mini-tubers evaluated per line.
[2] = average of 5 tubers evaluated per line. Tubers were from same source as those used for Phytophthora infestans isolate US8 inoculations.
[3] = average of 6 tuber slices (one slice per tuber; 6 tubers total) evaluated per line.

Example 7

Evaluation of Ranger Russet Lines in a Late Blight Field Trial

Three of the six Gemini lines described in Example 6 were chosen for a late blight resistance field trial, based upon their significant greenhouse and field-level reduction of tuber PPO activity level plus their resistance to black spot bruise, as demonstrated in Tables 2–4 of Example 6. The objective of the study was to determine if 'low PPO', black spot braise resistant Ranger Russet lines exhibit field level resistance to *P. infestans*, the causal agent of late blight.

FG1 seed of transgenic Ranger Russet lines Gemini 087, Gemini 108, Gemini 200, and standard nontransgenic Ranger Russet was produced at the same certified seed facility in Islands Falls, Me. as mentioned in Example 6. The seed was planted in early June in a randomized complete block design at the Brown Horticultural Research Farm near Corvallis, Oreg. Individual plots consisted of single rows, 25 hills in length, replicated 4 times. Potato plants were not treated with fungicides, and foliar infection by *P. infestans* developed by late August. Foliar disease levels were rated periodically through the remainder of the season, until vine kill in mid September. At harvest on September 28$^{th}$, all tubers were lifted to the soil surface and evaluated for visual symptoms of late blight infection. Healthy and blighted tubers were weighed separately, and the percentage blighted tubers was determined by dividing the fresh weight of blighted tubers by the total weight of all tubers.

The results of the tuber evaluation are presented in Table 5. All three transgenic Gemini lines exhibited significantly lower percentages of late blight infected tubers than Ranger Russet control. The level of late blight resistance was similar in all three Gemini lines. The field trial confirms that black spot bruise resistant Ranger Russet lines, which have a reduction in tuber PPO level, have increased field resistance to tuber infection by *P. infestans*, the causal agent of late blight. The field level resistance to late blight pathogen *P. infestans* by the transgenic 'low PPO', black spot bruise resistant tubers correlates with the resistance observed for the tuber inoculation studies described in Examples 5 and 6.

TABLE 5

The affect of natural field infection by *P. infestans* on incidence of late blight tuber infection in transgenic Ranger Russet potato lines, Corvallis, OR - 2000.

| Line | Total tuber wt per plot (lbs) | Wt of infected tubers (lbs) | % Late blight infected tubers |
|---|---|---|---|
| Ranger | 26.7 | 4.5 | 17.0 |
| Gemini 087 | 24.6 | 1.0 | 4.9 |
| Gemini 108 | 26.9 | 0.8 | 3.2 |
| Gemini 200 | 25.7 | 1.4 | 5.3 |
| LSD (p = 0.05) | NS | 2.0 | 8.5 |

Transgenic potato tubers generally containing less than 25% of wild-type PPO levels display enhanced resistance against *P. infestans*. Further evidence in support of this comes from late blight disease tests on tubers from transgenic Ranger Russet lines which are transformed with the smADPGPP promoter, or the SpoA promoter, driving antisense expression of the RR-PPO (constructs pMON21652 and pMON21656, respectively). Tuber PPO analyses of transgenic Ranger Russet events, transformed with pMON21562 or pMON21656 have identified populations of lines with tuber PPO activity levels reduced by 50–100% when compared to the wild type control (data not shown). In these tubers, significantly enhanced levels of late blight resistance were observed when PPO levels were reduced by 50% or greater, which indicates that other promoters such as the smADPGPP and SpoA promoters may perform equally as well, and even better than the GBSS and TFM7 promoters in terms of disease resistance.

Example 8

Use of dsRNA Method

For plant vector construction, a nearly full length RR-PPO deletion gene was created within the unique HindIII and NruI sites of the RR-PPO open-reading-frame, in which the first six nucleotides at the 5' end of the open-readingframe were omitted, and the last 148 nucleotides at the 3' end were omitted. The resultant RR-PPO deletion sequence consisted of a 5'-HindIII, 3'-NruI gene fragment composed 1638 nucleotides. This RR-PPO deletion sequence was fused to an exact copy of itself at its 3' end by ligation of the NruI sites of both fragments. The resultant inverted repeat RR-PPO deletion sequence, otherwise referred to as the "double-PPO gene" was cloned behind the promoter for the small subunit of the ADP-glucose pyrophosphorylase gene from potato, in a double-bordered binary *Agrobacterium* vector, which contained the CP4 EPSP synthase gene cassette for selection of transgenic plants on a glyphosate-containing medium. The resultant vector, pMON38293, now contained the double-PPO gene cassette as follows: smAD-PGPP/sensePPO-antisensePPO/E93'. See FIG. 5 for the plasmid map of pMON38293.

Potato cultivar Ranger Russet was transformed with pMON38293 via *Agrobacterium*—mediated transformation using glyphosate selection transformation, generally as described above. Ranger Russet pMON38293 transgenic lines were assigned the field name "Peru".

Two populations of Peru Ranger Russet lines transformed with pMON38293 were evaluated for tuber PPO activity. The first group consisted of 30 lines, while the second group consisted of 23 lines. The results of the PPO tyrosine and catechol assays, as well as the percent reduction in PPO activity from the Ranger Russet control based upon the specific activity of the catechol assay, are presented in Table 6.

TABLE 6

| Line # | Tyrosine Assay | Catechol Assay Spec. Act. | % Reduc. Activity From Control |
|---|---|---|---|
| Assay Request 55 | | | |
| Control | 5 | 0.511 | |
| Control | 5 | 0.510 | |
| 10533 | 0 | 0.001 | 99.8 |
| 10534 | 0 | 0.003 | 99.4 |
| 10535 | 5 | 0.412 | 19.4 |
| 10536 | 0 | 0.005 | 99.0 |
| 10537 | 0 | 0.026 | 94.9 |
| 10538 | 0 | 0.015 | 97.1 |
| 10539 | 5 | 0.456 | 10.8 |
| 10540 | 0 | 0.006 | 98.8 |
| 10541 | 0 | 0.021 | 95.9 |
| 10542 | 0 | 0.038 | 92.6 |
| 10543 | 0 | 0.025 | 95.1 |
| 10544 | 0 | 0.005 | 99.0 |
| 10546 | 0 | 0.004 | 99.2 |
| 10547 | 3 | 0.511 | 0.0 |
| 10548 | 0 | 0.034 | 93.3 |
| 10549 | 0 | 0.002 | 99.6 |
| 10550 | 0 | 0.041 | 92.0 |
| 10551 | 0 | 0.005 | 99.0 |
| 10552 | 3 | 0.365 | 28.6 |
| 10554 | 0 | 0.006 | 98.8 |
| 10555 | 0 | 0.003 | 99.4 |
| 10556 | 0 | 0.005 | 99.0 |
| 10557 | 0 | 0.005 | 99.0 |
| 10558 | 0 | 0.004 | 99.2 |
| 10559 | 0 | 0.008 | 98.4 |
| 10560 | 0 | 0.013 | 97.5 |
| 10561 | 0 | 0.022 | 95.7 |
| 10562 | 0 | 0.021 | 95.9 |
| 10563 | 0 | 0.004 | 99.2 |
| 10564 | 0 | 0.003 | 99.4 |
| Assay Request 58 | | | |
| Control | 5 | 0.336 | |
| Control | 5 | 0.339 | |
| 10565 | 0 | 0.002 | 99.4 |
| 10567 | 0 | 0.004 | 98.8 |
| 10568 | 0 | 0.010 | 97.0 |
| 10569 | 0 | 0.020 | 94.0 |
| 10570 | 0 | 0.010 | 97.0 |
| 10572 | 0 | 0.020 | 94.0 |
| 10573 | 5 | 0.346 | −3.0 |
| 10574 | 1 | 0.020 | 94.0 |
| 10575 | 4 | 0.238 | 29.2 |
| 10576 | 0 | 0.020 | 94.0 |
| 10577 | 0 | 0.007 | 97.9 |
| 10580 | 0 | 0.040 | 88.1 |
| 10581 | 0 | 0.020 | 94.0 |
| 10582 | 0 | 0.010 | 97.0 |
| 10584 | 0 | 0.050 | 85.1 |
| 10585 | 1 | 0.050 | 85.1 |
| 10586 | 5 | 0.159 | 52.7 |
| 10587 | 0 | 0.010 | 97.0 |
| 10588 | 0 | 0.040 | 88.1 |
| 10589 | 0 | 0.040 | 88.1 |
| 10590 | 0 | 0.010 | 97.0 |
| 10591 | 0 | 0.040 | 88.1 |
| 10592 | 0 | 0.040 | 88.1 |

The results indicate that 46 out of 53 total independent transgenic events (lines), or 87%, have 85% or better reduction in tuber PPO specific activity (catechol assay), and that 39 out of 53 total lines, or 74%, have 90–100% reduction in tuber PPO specific activity (catechol assay), as compared to the wild type Ranger Russet control. Many lines demonstrate nearly 100% reduction in tuber PPO specific activity. The results of the tyrosine assay also closely correlate with those of the catechol assay in that lines which had high values of oxidative browning also had high PPO specific activities by the catechol assay.

It is to be understood that the present invention has been described in detail by way of illustration and example in order to acquaint others skilled in the art with the invention, its principles, and its practical application. Particular aspects and methods of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

REFERENCES

The following are hereby incorporated by reference:

Ayub et al., *Nature Biotechnol.* 14: 862–866, 1996
Baulcombe et al., *Current Opinion Biotechnol.* 7: 173–180, 1996
Bell et al., *Proc. Natl. Acad. Sci. U.S.A.* 92: 8675–8679, 1995
Bird et al., *Biotechnol.* 9: 635–639, 1991

Bostock et al., Phytopathology 87: S10 (1997)
Brussian et al., *Plant Cell* 5: 667–677, 1993
Cheung et al., *Cell* 82: 383–393, 1995
Colombo et al., *Plant Cell* 9: 703–715 (1997)
Constabel et al., Proc Natl Acad Sci USA January 17;92(2): 407–11 (1995).
Corsini et al., Am. Pot. J. 69:423–434 (1992).
Craft, Am. Pot. J. 43:112–121 (1966)
Ecker et al., *Proc. Natl. Acad. Sci. U.S.A.* 83: 5372–5376, (1986).
Elkind et al., *Proc. Natl. Acad. Sci. U.S.A.* 87: 9057–9061.
Faske et al., *Plant Physiol.* 115: 705–715, 1997
Felton et al., J Insect Physiol 35, 981–990 (1989)
Fujiwara et al., *Plant Mol. Biol.* 20: 1059–1069, (1992)
Garcia-Olmedo et al., Biopolymers 47: 479–91, (1998).
Hamilton et al., *Nature* 346: 284–287, 1990
Hunt et al., Plant Molecular Biol. 21: 59–68 (1993).
Jarret et al., Physiol Plant 49:177–184 (1980).
Jarret et al., In Vitro 17:825–830 (1981).
Jorgensen and Napoli, U.S. Pat. No. 5,034,323 (1991).
Jorgensen and Napoli, U.S. Pat. No. 5,231,020 (1993).
Jorgensen and Napoli, U.S. Pat. No. 5,283,184 (1994).
Kening et al., The Plant Cell 7:1787–1799 (1995).
Landeo et al., In: *Phytophthora infestans* (ed. Dowley L J et al., Bole Press Ltd. Dublin, Ireland) pp. 268–274 (1995).
Maher et al., Proc. Natl. Acad. Sci. USA 91, 7802–7806 (1994).
Matzke et al., *Plant Physiol.* 107: 679–685 (1995)
Meyer et al., *Annu. Rev. Plant Physiol. Plant Mol. Biol.* 47: 23–48 (1996)
Montalbani et al., Physiol. Plant Pathol. 18, 51–57 (1981).
Nakata and Okita, Mol Gen Genet, 250:581–592 (1996).
Napoli et al., *Plant Cell* 2: 279–289 (1990).
Newman, et al., Plant Mol. Biol. 21:1035–1051 (1993).
Oeller et al., *Science* 254: 437–439 (1991).
Plakidou-Dymock et al., *Current Biol.* 8: 315–324 (1998).
Robinson and Dry, PCT patent application, WO 93/02195 (1993)
Rodermel et al., *Cell* 55: 673–681 (1988).
Rothstein et al., *Proc. Natl. Acad. Sci. U.S.A.* 84: 8439–8943 (1987).
Schaller et al., *Bioessays* 18: 27–33 (1996).
Smith et al., *Nature* 334: 724–726 (1988).
Smith et al., Planta 151, 535–540 (1981).
Smyth et al., *Current Biol.* 7: 793–795 (1997).
Santino et al., Plant Mol Biol, 33:405–416 (1997).
Shewmaker et al., U.S. Pat. No. 5,107,065 (1992).
Stark et al., Am. Pot. J. 62:657–666 (1985).
Steffens et al., in: Hedin Pa. (ed) Naturally Occurring Pest Bioregulators, 136–149. Am. Chem Soc, Washington, D.C. (1991).
Steffens, PCT publication, WO 93/15599 (1993).
Stockhaus et al., *EMBO J.* 9: 3013–3021 (1990).
Takahashi et al., *Plant J.* 11: 993–1005 (1997).
Thomma et al., et al., Proc. Natl. Acad. Sci. USA 95, 15107–11 (1998).
Thygesen, et al., Plant Physiol. 109:525–531 (1995).
Tingey http://www.nal.usda.gov/pgdic/pggrantinfo/1991/9156840.html (1993)
Trevanion et al., *Plant Physiol.* 113: 1153–1163 (1997)
Tsai et al., *Plant Physiology* 117: 101–112 (1998)
van der Krol et al., *Nature* 333: 866–869 (1988).
van der Krol et al., *Plant Molecular Biology* 14: 457–466 (1990).
Visser et al., *Mol. Gen. Genet.* 225: 289–296 (1991).
Waffenschmidt et al., Plant Cell, July; 5(7):809–20 (1993).
Wang et al., Phytopathology 87: S101 (1997).
Waterhouse et al., *Proc. Natl. Sci. USA,* 95:13959–13964, 1988.
Waterhouse et al., *Plant Mol. Biol.,* 43:67–82, 2000.
Yamasaki and Grace, FEBS Lett. February 6;422(3):377–80 (1998).
Yoshino and Murakami, Anal Biochem March 1;257(1): 40–4. (1998).
Zabeau and Bachem, PCT publication, WO 94/03607 (1994)

The invention claimed is:

1. A method of reducing polyphenol oxidase activity in a plant comprising: transforming the plant with a transgene encoding a dsRNA, said transgene comprising a first sequence as set forth in SEQ ID NO: 1 and a second sequence as set forth in SEQ ID NO: 2, wherein said transgene is expressed in said plant.

2. The method of claim 1 wherein said plant is a potato plant.

3. A plant comprising a transgene encoding a dsRNA, said transgene comprising a first sequence as set forth in SEQ ID NO: 1 and a second sequence as set forth in SEQ ID NO: 2, wherein said transgene is expressed in said plant.

4. Progeny or seed of the plant of claim 3, wherein said progeny or seed comprise said transgene.

5. The plant of claim 3, wherein said plant is a potato plant.

6. Progeny of the plant of claim 5, wherein said progeny comprise said transgene.

7. A method for reducing susceptibility of a plant to disease comprising: transforming the plant with a transgene encoding a dsRNA, said transgene comprising a first sequence e as set forth in SEQ ID NO: 1 and a second sequence as set forth in SEQ ID NO: 2, wherein said transgene is expressed in said plant.

8. A method for reducing susceptibility of potato to bruising comprising: transforming the plant with a transgene encoding a dsRNA, said transgene comprising a first sequence e as set forth in SEQ ID NO: 1 and a second sequence as set forth in SEQ ID NO: 2, wherein said transgene is expressed in said plant.

* * * * *